(12) United States Patent
Higashi et al.

(10) Patent No.: US 11,193,948 B2
(45) Date of Patent: Dec. 7, 2021

(54) REAGENT KIT AND METHOD FOR DERIVATIZING AND QUANTIFYING VITAMIN D USING A MASS SPECTROMETER

(71) Applicants: Tokyo University of Science, Tokyo (JP); National University Corporation Chiba University, Chiba (JP); JEOL Ltd., Tokyo (JP)

(72) Inventors: Tatsuya Higashi, Kashiwa (JP); Shoujiro Ogawa, Kashiwa (JP); Fumio Nomura, Chiba (JP); Mamoru Satoh, Chiba (JP); Masaki Takiwaki, Chiba (JP)

(73) Assignees: Tokyo University of Science, Tokyo (JP); National University Corporation Chiba University, Chiba (JP); JEOL Ltd., Tokyo (JP)

( * ) Notice: Subject to any disclaimer, the term of this patent is extended or adjusted under 35 U.S.C. 154(b) by 522 days.

(21) Appl. No.: 15/813,542

(22) Filed: Nov. 15, 2017

(65) Prior Publication Data

US 2018/0136240 A1 May 17, 2018

(30) Foreign Application Priority Data

Nov. 17, 2016 (JP) .............................. JP2016-224171

(51) Int. Cl.
*G01N 33/82* (2006.01)
*G01N 30/72* (2006.01)

(52) U.S. Cl.
CPC ............ *G01N 33/82* (2013.01); *G01N 30/72* (2013.01); *G01N 2458/15* (2013.01); *G01N 2560/00* (2013.01)

(58) Field of Classification Search
CPC .......................... G01N 33/82; G01N 2458/15
See application file for complete search history.

(56) References Cited

U.S. PATENT DOCUMENTS

| | | | | |
|---|---|---|---|---|
| 10,761,102 B2* | 9/2020 | Higashi | .................. | G01N 33/82 |
| 2013/0137185 A1* | 5/2013 | Holmquist | ............. | G01N 33/82 |
| | | | | 436/140 |

(Continued)

FOREIGN PATENT DOCUMENTS

| | | |
|---|---|---|
| JP | 2015166740 A | 9/2015 |
| WO | 2011072152 A1 | 6/2011 |

OTHER PUBLICATIONS

Higashi, T. et al. "A Method for Simultaneous Determination of 25-Hydroxyvitamin D3 and Its 3-Sulfate in Newborn Plasma by LC/ESI-MS/MS after Derivatization with a Proton-Affinitive Cookson-Type Reagent," Mass Spectrom (Tokyo) 2016; 5(2): S0051. Epub Aug. 31, 2016 (Year: 2016).*

(Continued)

*Primary Examiner* — Christopher Adam Hixson
*Assistant Examiner* — Michelle Adams
(74) *Attorney, Agent, or Firm* — The Webb Law Firm

(57) ABSTRACT

Provided is a method for quantifying vitamin D, with the vitamin D contained in a biological sample being derivatized with a derivatization reagent and being measured with a mass spectrometer, the method including, a derivatization step of derivatizing n number of samples by using n types of 4-(4'-dimethylaminophenyl)-1,2,4-triazoline-3,5-dione (DAPTAD) isotopologues respectively as derivatization reagents, a mixing step of mixing the n types of derivatization samples obtained in the derivatization step, and a quantitative analysis step of subjecting each of the n types of (Continued)

vitamin D derivatives contained in the mixed sample obtained in the mixing step to quantitative analysis using a mass spectrometer.

9 Claims, 14 Drawing Sheets

(56) References Cited

U.S. PATENT DOCUMENTS

2016/0061848 A1 3/2016 Holmquist et al.
2017/0261523 A1 9/2017 Holmquist et al.
2018/0088137 A1 3/2018 Higashi et al.

OTHER PUBLICATIONS

Higashi, T. et al. "Usefulness of Derivatization in High-Performance Liquid Chromatography/Tandem Mass Spectrometry of Conjugated Vitamin D Metabolites," Analytical Sciences Jul. 1999, Vo.. 15, 619-623. (Year: 1999).*

Gao, C. et al. "Simultaneous quantification of 25-hydroxyvitamin D3-3-sulfate and 25-hydroxyvitamin D3-3-glucuronide in human serum and plasma using liquid chromatography-tandem mass spectrometry coupled with DAPTAD-derivatization," Journal of Chromatography B 1060 (2017) 158-165. Online Jun. 9, 2017 (Year: 2017).*

Waters Co. "Solvents and Caveats for LC/MS" archived by the Internet Archive Wayback Machine on Jun. 24, 2013, obtained by the examiner of U.S. Appl. No. 15/718,809 at <http://web.archive.org/web20130624072312/http://www.waters.com/waters/en_US/Solvents-and-Caveats-for-LC-MS/nav.htm?cid=10091173&locale=en US> on Mar. 29, 2019. (Year: 2013).

Office Action issued in U.S. Appl. No. 15/718,809 dated Apr. 4, 2019.

Ogawa et al., "A novel Cookson-type reagent for enhancing sensitivity and specificity in assessment of infant vitamin D status using liquid chromatography/tandem mass spectrometry", Rapid Commun. Mass Spectrom., 2013, pp. 2453-2460, 27.

Extended European Search Report for application No. 17193756.8 dated Jan. 11, 2018.

Ogawa et al., "Comparative evaluation of new Cookson-type reagents for LC/ESI-MS/MS assay of 25-hydroxyvitamin D3 in neonatal blood samples", Biomedical Chromatography, Jun. 1, 2016, vol. 30, No. 6, pp. 938-945, GB.

Ding et al., "Quantitative determination of vitamin D metabolites in plasma using UHPLC-MS/MS", Analytical and Bioanalytical Chemistry, Jul. 14, 2010, vol. 398, No. 2, pp. 779-789.

Tatsuya et al., "A specific LC/ESI-MS/MS method for determination of 25-hydroxyvitamin D3 in neonatal dried blood spots containing a potential interfering metabolite, 3-epi-25-hydroxyvitamin D3", Journal of Separation Science, Apr. 1, 2011, vol. 34, No. 7, pp. 725-732.

Ogawa et al., "Analysis of urinary vitamin D3 metabolites by liquid chromatography/tandem mass spectrometry with ESI-enhancing and stable isotope-coded derivatization", Analytical and Bioanalytical Chemistry, Aug. 29, 2014, vol. 406, No. 26, pp. 6647-6654.

Ogawa et al., "Enhancing analysis throughput, sensitivity and specificity in LC/ESI-MS/MS assay of plasma 25-hydroxyvitamin D3 by derivation with triplex 4-(4-dimethylaminophenyl)-1, 2,4-triazoline-5, 5-dione (DAPTAD) isotopologues", Journal of Pharmaceutical and Biomedical Analysis, Nov. 17, 2016, vol. 136, No. 17, pp. 126-133.

Office Action issued in U.S. Appl. No. 15/718,809 dated Dec. 20, 2019.

Office Action issued in JP2016-190684 dated May 12, 2020.

Office Action issued in JP 2016-190684 dated Dec. 15, 2020.

* cited by examiner

REAGENT KIT AND METHOD FOR DERIVATIZING AND QUANTIFYING VITAMIN D USING A MASS SPECTROMETER

Japanese Patent Application No. 2016-224171, filed on Nov. 17, 2016, is hereby incorporated by reference in its entirety.

BACKGROUND OF THE INVENTION

The present invention relates to a method for quantifying vitamin D, a mass spectrometer, and a reagent kit for quantifying vitamin D.

Analysis with a mass spectrometer (hereinafter sometimes referred to as "MS") is known, for example, in a clinical examination at a hospital. In particular, analysis of a substance derived from a biological body, for example, a hormone with a liquid chromatograph mass spectrometer (hereinafter sometimes referred to as "LC/MS"), which involves separating a compound by high performance liquid chromatography (HPLC) and ionizing and analyzing the separated substance with the MS, has high sensitivity and high specificity as compared to immunoassay and the like that have hitherto been used. Further, the above-mentioned analysis is capable of performing simultaneous analysis of a number of items. Therefore, the above-mentioned analysis is rapidly becoming used widely in recent years. In quantitative analysis, particularly, with an LC/MS/MS using a tandem mass spectrometer (hereinafter sometimes referred to as "MS/MS"), a plurality of substances can be selectively subjected to quantitative analysis with a selected reaction monitoring (hereinafter sometimes referred to as "SRM") mode having sensitivity higher than that of the LC/MS.

In recent years, as one example of the analysis of a substance derived from a biological body with the LC/MS/MS, analysis of vitamin D (hereinafter sometimes referred to as "V.D.") and vitamin D metabolites in the blood is drawing attention. Vitamin D, which is an s-cis-diene compound, and is a fat-soluble vitamin necessary for regulating calcium metabolism, has an action of increasing the concentration of calcium ($Ca^{2+}$) in the blood as activated vitamin D ($1\alpha,25$-dihydroxyvitamin D, hereinafter sometimes referred to as "$1,25(OH)_2D$"). In addition to the above-mentioned action, in vivo metabolites such as $1,25(OH)_2D$ and 25-hydroxyvitamin D (hereinafter sometimes referred to as "25(OH)D") play important roles in controlling expression of proteins involved in differentiation and growth of cells, production and secretion of a hormone, an immune reaction, and the like. Therefore, vitamin D is classified as a hormone in some cases from the viewpoints of the action mechanism and the function.

As described above, vitamin D and vitamin D metabolites (hereinafter sometimes collectively referred to as "vitamin D") have bioactivity in a wide range as well as roles as nutrients, and the excess or deficiency of vitamin D is considered to increase the morbidity of various diseases. Therefore, the number of cases of measurement of vitamin D in the blood is increasing. Additionally, because of its high sensitivity, high specificity and accurate analysis, analysis of vitamin D using the LC/MS/MS is also used.

An atmospheric pressure chemical ionization (APCI) and an electrospray ionization (ESI) and the like are used as an ionization method used in the LC/MS/MS. The ESI is an ionization method that is most generally used in the LC/MS/MS by virtue of the smallest risk of causing fragmentation, a wide range of applicable compounds, and high operability. However, in general, because of the low ESI responsiveness to the vitamin D metabolites and the low content of it in the blood, the sensitivity of the method may be insufficient even if the LC/MS/MS is used for the analysis. In view of the foregoing, in order to enhance the detection sensitivity in the LC/MS/MS by increasing the ionization efficiency of the vitamin D metabolites, for example, the vitamin D metabolites are analyzed in some cases after being derivatized with 4-phenyl-1,2,4-triazoline-3,5-dione (PTAD) that is one of Cookson-type derivatization reagents (see, for example, Japanese Patent Application Publication No. 2015-166740). Derivatization of vitamin D with PTAD improves the sensitivity which compared to before derivatization, and enables to perform highly selective detection.

However, further improvement in sensitivity is desired in order to measure a small amount of a sample, for example, blood collected from a newborn baby. For this reason, the inventors of the present invention have developed, as a novel Cookson-type derivatization reagent, 4-(4'-dimethylaminophenyl)-1,2,4-triazoline-3,5-dione (DAPTAD) (see, for example, S. Ogawa, et al., Rapid Commun. Mass Spectrom., 25, 2453-2460 (2013)). Vitamin D derivatized with DAPTAD has signal intensity increased by about 100 times that before derivatization, and the derivatization with DAPTAD is suitable for analyzing a small amount of a sample with the LC/MS/MS. The signal intensity obtained by the derivatization with DAPTAD is about 10 times that obtained by the derivatization with PTAD that has hitherto been used. Further, derivatizing 25(OH)D, which is one of the vitamin D metabolites with DAPTAD enables to distinguish and quantitate structural isomers such as C3-epimer (3-epi-25(OH)D), which are inactive interference metabolites, and the selectivity is improved than before.

As described above, the derivatization of vitamin D with DAPTAD is particularly effective for assiduous diagnosis of neonatal blood vitamin D deficiency of the neonatal blood since analysis with the LC/ESI-MS/MS enables accurate analysis with a small amount. On the other hand, in analysis with the LC/ESI-MS/MS, the enhancement of the analysis throughput is desired.

SUMMARY

According to embodiments of the present invention, there can be provided a method for quantifying vitamin D, a mass spectrometer, and a reagent kit for quantifying vitamin D in which enable accurate analysis with a small amount of sample and enable to enhance the analysis throughput.

According to a first aspect of the present invention, there is provided a method for quantifying vitamin D, with the vitamin D contained in a biological sample being derivatized with a derivatization reagent and being measured with a mass spectrometer, the method including:

a derivatization step of derivatizing n number of samples by using n types of 4-(4'-dimethylaminophenyl)-1,2,4-triazoline-3,5-dione (DAPTAD) isotopologues respectively as derivatization reagents;

a mixing step of mixing the n types of derivatization samples obtained in the derivatization step, and a quantitative analysis step of subjecting each of the n types of vitamin D derivatives contained in the mixed sample obtained in the mixing step to quantitative analysis using a mass spectrometer.

According to a second aspect of the present invention, there is provided a mass spectrometer including:

a separation unit that separates vitamin D derivatives from a mixed sample of n number of derivatization samples having different masses respectively derivatized by n types of 4-(4'-dimethylaminophenyl)-1,2,4-triazoline-3,5-dione (DAPTAD) isotopologues having different masses, an ionization unit that ionizes the vitamin D derivatives separated in the separation unit, a mass separation unit that separates and detects ions generated in the ionization unit according to mass, and a calculation unit that quantifies the n types of vitamin D derivatives having different masses, detected by separation in the mass separation unit, in association with the amounts of the n types of vitamin D derivatives contained in the mixed sample, based on the respective amounts of ions detected.

According to a third aspect of the present invention, there is provided a reagent kit for quantifying vitamin D, the derivatization reagent kit including: n types of 4-(4'-dimethylaminophenyl)-1,2,4-triazoline-3,5-dione (DAPTAD) isotopologues; a derivatization reaction stopping agent; and a decomposition inhibitor of a derivative.

DETAILED DESCRIPTION OF THE EMBODIMENT

Figure 1:
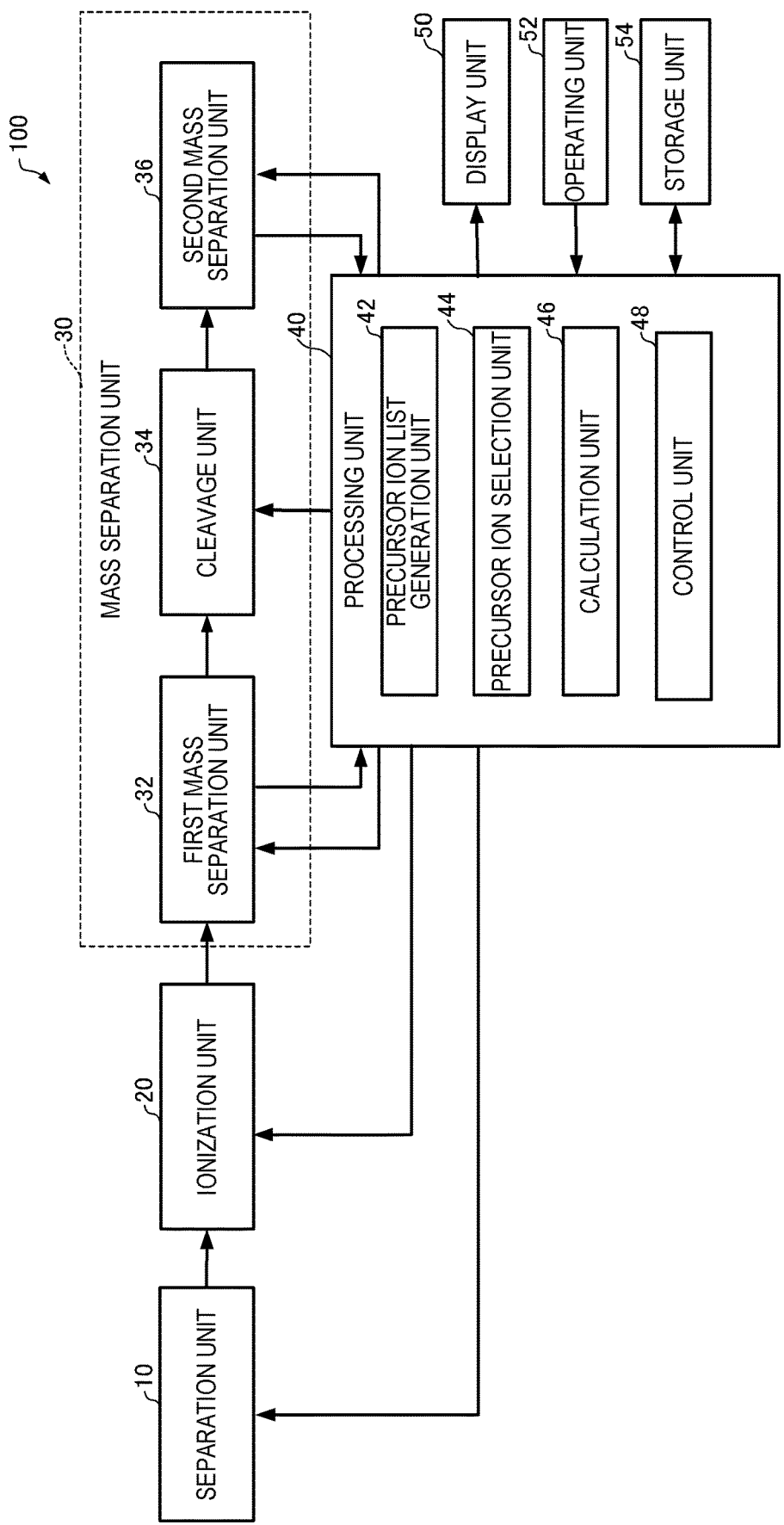
FIG. 1 is a drawing schematically indicating the configuration of a mass spectrometer according to one embodiment of the present invention.

According to one embodiment of the present invention, there is provided a method for method for quantifying vitamin D, with the vitamin D contained in a biological sample being derivatized with a derivatization reagent and being measured with a mass spectrometer, the method including:

a derivatization step of derivatizing n number of samples by using n types of 4-(4'-dimethylaminophenyl)-1,2,4-triazoline-3,5-dione (DAPTAD) isotopologues respectively as derivatization reagents;

a mixing step of mixing the n types of derivatization samples obtained in the derivatization step, and a quantitative analysis step of subjecting each of the n types of vitamin D derivatives contained in the mixed sample obtained in the mixing step to quantitative analysis using a mass spectrometer.

In the above-mentioned method, by using n types of DAPTAD isotopologues, which are identical molecules and different only in isotope composition, as the derivatization reagent, the selectivity of analysis with the mass spectrometer is improved, and simultaneous quantitative analysis of the n types of samples can be performed in one measurement. Therefore, it is possible to accurate analysis with a small amount of the n types samples, and enable to enhance the analysis throughput.

According to one embodiment of the present invention, there is provided a mass spectrometer including:

a separation unit that separates vitamin D derivatives from a mixed sample of n number of derivatization samples having different masses respectively derivatized by n types of 4-(4'-dimethylaminophenyl)-1,2,4-triazoline-3,5-dione (DAPTAD) isotopologues having different masses, an ionization unit that ionizes the vitamin D derivatives separated in the separation unit, a mass separation unit that separates and detects ions generated in the ionization unit according to mass, and a calculation unit that quantifies the n types of vitamin D derivatives having different masses, detected by separation in the mass separation unit, in association with the amounts of the n types of vitamin D derivatives contained in the mixed sample, based on the respective amounts of ions detected.

In the above-mentioned mass spectrometer, by using n types of DAPTAD isotopologuesas as the derivatization reagent, the selectivity of analysis with the mass spectrometer is improved, and simultaneous quantitative analysis of the n types of samples can be performed in one measurement. Therefore, it is possible to accurate analysis with a small amount of the n types samples, and enable to enhance the analysis throughput.

According to one embodiment of the present invention, there is provided a derivatization reagent kit for quantifying vitamin D including:

n types of 4-(4'-dimethylaminophenyl)-1,2,4-triazoline-3,5-dione (DAPTAD) isotopologues having different masses;
a derivatization reaction stopping agent; and
a decomposition inhibitor of a derivative.

In the above-mentioned derivatization reagent kit, by using n types of DAPTAD isotopologues as a derivatization reagent, the selectivity of analysis with the mass spectrometer is improved, and simultaneous quantitative analysis of the n types of samples can be performed in one measurement. Therefore, it is possible to accurate analysis with a small amount of the n types samples, and enable to enhance the analysis throughput. Further, the derivatization reagent kit comprising a derivatization reaction stopping agent and a decomposition inhibitor of a derivative, the decomposition of the derivative to be obtained can be suppressed, and more accurate analysis has become possible.

Preferred embodiments of the present invention are described in detail below with reference to the drawings. The following embodiments do not unduly limit the present invention as stated in the claims. In addition, all of the elements described below should not necessarily be taken as essential elements of the present invention.

1. Mass Spectrometer

First, an explanation is provided of the configuration of a mass spectrometer according to one embodiment of the present invention with reference to the drawings. FIG. 1 is a drawing schematically indicating the configuration of a mass spectrometer 100 according to the present embodiment.

As shown in FIG. 1, the mass spectrometer 100 is composed of a separation unit 10, an ionization unit 20, a mass separation unit 30, a processing unit 40, a display unit 50, an operating unit 52 and a storage unit 54. Moreover, the mass separation unit 30 is composed of a first mass separation unit 32, a cleavage unit 34 and a second mass separation unit 36.

The mass spectrometer 100 is a tandem (MS/MS) mass spectrometer provided with the cleavage unit 34 between the two mass separation units 32 and 36. In the mass spectrometer 100, an ion of a specific mass number (precursor ion) is extracted in the first mass separation unit 32 and led to the cleavage unit 34, and secondary ions (fragment ions) generated from the precursor ion selected in the first mass separation unit 32 are detected in the second mass separation unit 36.

The sample serving as the analysis target of the mass spectrometer 100 is a mixed sample of n types of derivatization samples having different masses obtained by pretreating, for instance, biological samples containing vitamin D and vitamin D metabolites followed by derivatizing the samples with n types of derivatization reagents (DAPTAD isotopologues) having different masses to be subsequently described.

The separation unit 10 separates vitamin D derivatives from the mixed sample of n types of derivatization samples. For example, the separation unit 10 employs high-performance liquid chromatograph (which may also be referred to as "HPLC"), and the high-performance liquid chromatograph preferably employs reversed-phase distribution high-performance liquid chromatograph. During separation of vitamin D derivatives, the use of reversed-phase distribution high-performance liquid chromatograph enables the separation unit 10 to separate structural isomers such as 25(OH)$D_3$ and inactive interference metabolizes in the form of 3-epimers (3-epi-25(OH)$D_3$) in particular.

Although not shown in the drawings, the separation unit 10 is provided with a mobile phase container, a pump, an injector and a column. The mobile phase container stores a mobile phase. The pump aspirates the mobile phase stored in the mobile phase container and supplies the mobile phase to the column at a constant flow rate through the injector for loading a sample. The injector is provided with an auto sampler, for example, and loads a preliminarily adjusted prescribed amount of sample into the mobile phase. When a sample is loaded into the mobile phase by the injector, the sample is loaded into the column along with the mobile phase.

The mixed sample of n types of derivatization samples having different masses are separated into individual substances based on differences in the degrees of interaction of the substances present in the sample with the mobile phase and stationary phase with which the column is packed as the mixed sample passes through the column. The separated substances elute from the outlet of the column at different times. Namely, each separated substance has its own established retention time, and retention time is the amount of time from the time a sample is loaded into the mobile phase by the injector to the time the sample elutes from the column. The eluent is introduced into the ionization unit 20.

The ionization unit 20 ionizes vitamin D derivatives targeted for analysis that have been separated in the separation unit 10. Although there are no particular limitations on the ionization method used in the ionization unit 20, electrospray ionization (ESI) is used preferably. ESI is preferable since it is the least likely to cause fragmentation, can be applied to a wide range of compounds, and offers a high level of operability. Ions generated in the ionization unit 20 are introduced into the mass separation unit 30 in a state in which $H^+$ has been added to the analysis target M, and are separated and detected according to their mass.

The first mass separation unit 32 separates and detects ions generated in the ionization unit 20 according to the mass thereof. The first mass separation unit outputs information on detection results (mass spectral data) to the processing unit 40.

In addition, the first mass separation unit 32 selects specific ions and sends those ions to the cleavage unit 34. Ions selected in the first mass separation unit 32 are determined with a precursor ion selection unit 44 of the processing unit 40.

Examples of mass spectrometers that can be used for the first mass separation unit 32 include quadrupole (Q), time-of-flight (TOF), ion trap (IT), magnetic sector and Fourier-transform ion cyclotron resonance (FT-ICR) types of mass spectrometers.

The cleavage unit 34 cleaves precursor ions selected with the first mass separation unit 32. This results in the generation of fragment ions. Namely, fragment ions are ions obtained by cleaving precursor ions. Examples of the method used to cleave precursor ions in the cleavage unit 34 include collision-induced dissociation (CID) resulting from collision with gas and photodissociation by which the precursor ions are cleaved by irradiating with light. Furthermore, there are no particular limitations on the method used to cleave precursor ions in the cleavage unit 34.

The second mass separation unit 36 separates and detects fragment ions cleaved in the cleavage unit 34 according to the mass thereof. The second mass separation unit 36 outputs information on detection results (mass spectral data) to the processing unit 40.

Examples of mass spectrometers that can be used for the second mass separation unit 36 include quadrupole (Q), time-of-flight (TOF), ion trap (IT), magnetic sector and Fourier-transform ion cyclotron resonance (FT-ICR) types of mass spectrometers. Furthermore, the same type of mass spectrometer as that used for the first mass separation unit 32 may be used for the second mass separation unit 36, or a mass spectrometer different from that of the first mass separation unit 32 may be used. An example of a preferable combination of the first mass separation unit 32 and the second mass separation unit 36 used when identifying vitamin D consists of the use of quadrupole mass spectrometers for both the first mass separation unit 32 and the second mass separation unit 36.

The display unit 50 displays processing results of the processing unit 40 as a display signal in the form of text, graphs and other information based on a display signal input from the processing unit 40. The display unit 50 displays, for example, vitamin D identification results. The display unit 50 is, for example, a CRT, LCD or touch panel display.

The operating unit 52 carries out processing for acquiring an operation signal corresponding to an operation by a user and transmitting that signal to the processing unit 40. The operating unit 52 consists of, for example, buttons, keys, touch panel display or microphone.

The storage unit 54 stores programs or data and the like for allowing the processing unit 40 to carry out various types of computational and control processing. In addition, the storage unit 54 is also used as a work area of the processing unit 40 as well as temporarily store operation signals input from the operating unit 52 along with the results of calculations performed by the processing unit 40 in accordance with various programs.

The storage unit 54 also stores a vitamin D peak list (list of mass-to-charge ratios) for identifying vitamin D based on the results of MS/MS measurements.

The processing unit 40 carries out various calculations in accordance with a program stored in the storage unit 54. Functions of the processing unit 40 can be realized by programs and various types of processors (such as a CPU or DSP) and other hardware.

In the present embodiment, the processing unit (CPU) 40 functions as a precursor ion list generation unit 42, the precursor ion selection unit 44, a calculation unit 46 and a control unit 48 to be subsequently explained by running a program stored in the storage unit 54. However, at least a portion of the processing unit 40 may also be realized with hardware (dedicated circuitry).

The precursor ion list generation unit 42 generates a list of precursor ions based on detection results of the first mass separation unit 32. Here, a list of precursor ions refers to candidate ions for MS/MS measurement, or in other words, ions selected in the first mass separation unit 32.

More specifically, the precursor ion list generation unit 42 generates a list (list of m/z values) of peaks appearing in MS spectra obtained as a result of MS measurement in the first mass separation unit 32, and then uses this list as a list of precursor ions. Here, MS measurement refers to measurement of ions obtained by ionizing a sample in the ionization unit 20 that is carried out in the first mass separation unit 32. In addition, MS spectra refer to mass spectra (spectra represented by plotting m/z values on the horizontal axis and detection intensity on the vertical axis) obtained by MS measurement.

The precursor ion selection unit 44 selects ions from the list of precursor ions generated by the precursor ion list generation unit 42 and determines those ions selected in the first mass separation unit 32. Namely, those ions selected from the list of precursor ions by the precursor ion selection unit 44 are selected in the first mass separation unit 32 as precursor ions. For example, the precursor ion selection unit 44 selects ions from the list of precursor ions in order starting with the ion having the greatest peak intensity (detection intensity).

When the precursor ion selection unit 44 selects an ion from the list of precursor ions, the control unit 48 controls each of the units 10, 20 and 30 of the mass spectrometer 100 so that MS/MS measurement is carried out on the ion selected by the precursor ion selection unit 44. At this time, the ion selected in the precursor ion selection unit 44 is selected in the first mass separation unit 32 and controlled to as to be loaded into the cleavage unit 34. Here, MS/MS measurement refers to selecting a specific ion from among ions generation in the ionization unit 20 in the first mass separation unit 32 followed by spontaneously or forcibly cleaving that ion in the cleavage unit 34 and carrying out mass spectrometry in the second mass separation unit 36.

The calculation unit 46 quantifies the n types of vitamin D derivatives having different masses detected by separating in the mass separation unit 30, in other words, the n types of vitamin D derivatives having different masses obtained by MS/MS measurement, in association with the amounts of the n types of vitamin D derivatives contained in the mixed sample based on the respective amounts of ions detected. Namely, the calculation unit 46 assigns peaks to the n types of vitamin D derivatives having different masses separated as fragment ions in the second mass separation unit 36, carries out quantitative calculations based on the amount of ions (ion intensity) of each peak detected as a vitamin D derivative, calculates the amount of each of the n types of vitamin D derivatives contained in the mixed sample containing n number of derivatization samples, and carries out quantitative calculations on each vitamin D derivative contained in the n number of samples.

The calculation unit 46 compares the peak list (list of mass-to-charge ratios) obtained from the mass spectra (MS/MS spectra) obtained by MS/MS measurement with a peak list of derivatized vitamin D and vitamin D derivatives stored in the storage unit 54. For example, the calculation unit 46 selects a fragment ion of a vitamin D derivative from information contained in the peak list stored in the storage unit 54 and compares the results of MS/MS measurement with the peak list to identify the peak and quantify vitamin D based on the ion intensity of that peak.

Furthermore, the peak list can contain transitions, and transitions can be selected by operating the operating unit 52.

The control unit 48 controls the separation unit 10, the ionization unit 20 and the mass separation unit 30. MS measurement, MS/MS measurement and the like are carried out as a result of the control unit 48 controlling each of these units 10, 20 and 30.

2. A Method for Quantifying Vitamin D

Next, an explanation is provided of a method for quantifying vitamin D according to one embodiment of the present invention with reference to the drawings.

The method according to the present embodiment is a method for quantifying vitamin D, with the vitamin D contained in a biological sample being derivatized with a derivatization reagent and being measured with a mass spectrometer, the method including: a derivatization step of derivatizing n number of samples by using n types of 4-(4'-dimethylaminophenyl)-1,2,4-triazoline-3,5-dione (DAPTAD) isotopologues respectively as derivatization reagents; a mixing step of mixing the n types of derivatization samples obtained in the derivatization step, and a quantitative analysis step of subjecting each of the n types of vitamin D derivatives contained in the mixed sample obtained in the mixing step to quantitative analysis using a mass spectrometer.

Figure 2:
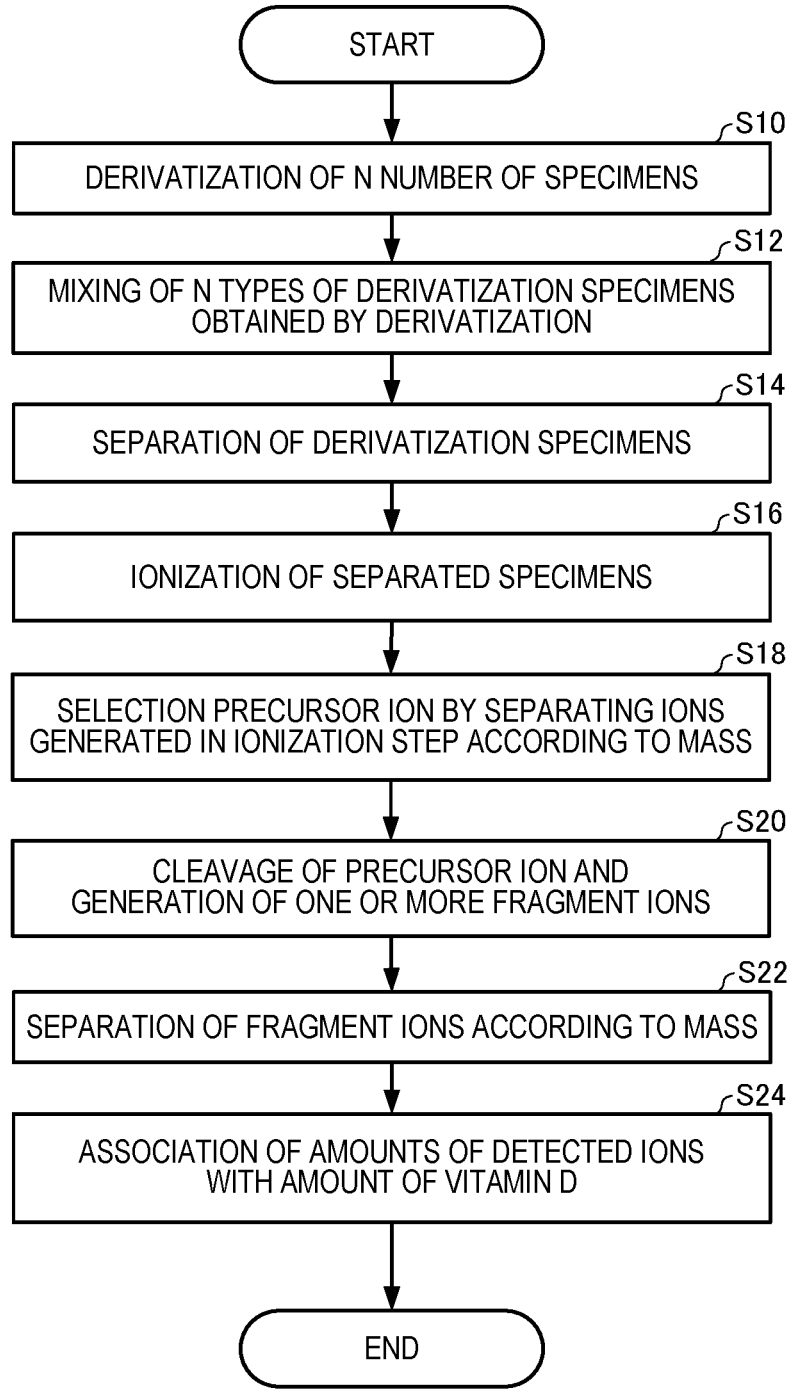
FIG. 2 is a flow chart indicating an example of a method for quantifying vitamin D according to one embodiment of the present invention.

FIG. 2 is a flow chart indicating an example of a method for quantifying vitamin D according to one embodiment of the present invention. Here, an explanation is provided of a method for quantifying vitamin D according to the embodiment of the present invention using the mass spectrometer 100 shown in FIG. 1.

The term "DAPTAD-derivative" as used herein refers to a compound that is formed by adding DAPTAD which is the Cookson-type derivatization reagent to an s-cis-diene moiety of vitamin D which is the s-cis-diene compound. Further, the term "derivatization" as used herein means adding DAPTAD which is the Cookson-type derivatization reagent to vitamin D which is the s-cis-diene compound to form a DAPTAD-derivative. Further, the term "derivatization reaction" as used herein refers to a reaction for causing DAPTAD which is the Cookson-type derivatization reagent to react with vitamin D which is the s-cis-diene compound to form a DAPTAD-derivative.

2.1. Derivatization Step

First, derivatizing n number of sample by using n types of 4-(4'-dimethylaminophenyl)-1,2,4-triazoline-3,5-dione (DAPTAD) isotopologues respectively as derivatization reagents, and derivatize vitamin D contained in a biological sample (Step S10). Specifically, n number of biological sample such as plasma or serum are collected and pretreated, and the obtained sample are derivated with different DAPTAD isotopologues respectively.

2.1.1. Vitamin D

A compound to be derivatized by the method according to this embodiment is vitamin D or vitamin D metabolites which are s-cis-diene compound. Vitamin D or vitamin D metabolites with an s-cis-diene moiety quantitatively react with the Cookson-type derivatization reagent described later by a Diels-Alder reaction to be derivatized, and can be subjected to quantitative analysis with high sensitivity and high selectivity, in particular, in the analysis with the LC-ESI-MS/MS.

Vitamin D belongs to secosteroid in broad classification, and is a collective term of vitamin $D_2$ derived from vegetable food and vitamin $D_3$ derived from animal food and skin production. Both vitamin $D_2$ and vitamin $D_3$ are homologues that differ only in side chain structure, and are considered to be similarly metabolized inside of a human body and to have equivalent bioactivity. Therefore, in this specification, vitamin $D_2$ and vitamin $D_3$ are not distinguished from each other and simply referred to as vitamin D. Further, in this specification, vitamin D and vitamin D metabolites are simply referred to as vitamin D, and vitamin D in this case refers to naturally-occurring or synthesized vitamin D or any one of molecular species related to vitamin D generated through transformation of vitamin D, such as intermediates and products of vitamin D metabolism.

Such molecular species of vitamin D is not particularly limited, and examples thereof include 25-hydroxy vitamin $D_3$ (25(OH)$D_3$), 25-hydroxy vitamin $D_2$ (25(OH)$D_2$), 1α,25-dihydroxy vitamin $D_3$ (1,25(OH)$_2D_3$), 23,25-dihydroxy vitamin $D_3$ (23,25(OH)$_2D_3$), 25,26-dihydroxy vitamin $D_3$ (25,26(OH)$_2D_3$), 24,25-dihydroxy vitamin $D_3$ (24,25(OH)$_2D_3$), and 4β,25-dihydroxy vitamin $D_3$ (4β,25(OH)$_2D_3$). The molecular species of vitamin D may be an isomer of the above-mentioned molecular species, and an example thereof is 3-epi-25-hydroxy vitamin $D_3$ (3-epi-25(OH)$D_3$). In addition, those molecular species of vitamin D may be sulfates, and an example thereof is 25-hydroxy vitamin $D_3$-3β-sulfate (25(OH)$D_3$S). In the quantitative analysis of vitamin D, a plurality of those molecular species of vitamin D may be contained.

2.1.2. DAPTAD

In the derivatization step according to this embodiment, the above-mentioned vitamin D and vitamin D metabolites are derivatized with DAPTAD which is a kind of the Cookson-type derivatization reagent. The Cookson-type derivatization reagent selectively reacts with s-cis-diene moiety of the compound to quantitatively form a derivative through the Diels-Alder reaction.

Figure 3:
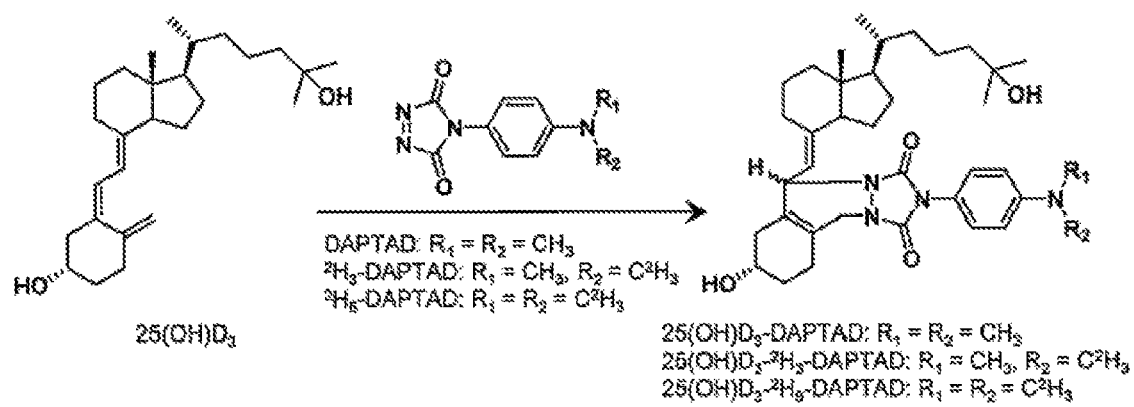
FIG. 3 is a diagram indicating a derivatization reaction scheme of $25(OH)D_3$ with DAPTAD.

As shown in FIG. 3, DAPTAD, that is, 4-(4'-dimethylaminophenyl)-1,2,4-triazoline-3,5-dione, is preferably used as the Cookson-type derivatization reagent for the method for quantifying vitamin D, from the viewpoints of sensitivity, selectivity, and stability.

In this embodiment, DAPTAD has n types of DAPTAD isotopologues. Isotopologues mean the same molecule differing only in the isotopic composition, that is, a plurality of molecular species having the same chemical composition, while having different molecular weights due to the different amounts of isotopes. Each isotopologue has a distinctive exact mass, but does not have a unique structure. Therefore, by using an isotope as a derivatizing reagent and using it as an isotopolog, the selectivity in analyzing the obtained derivative with a mass spectrometer is improved. In particular, in the SRM mode of the LC/ESI-MS/MS, it is possible to coordinate common ions, and ions that generate constant mass difference by comparing the MS/MS spectra. Thus, it is possible to simultaneously analyze a larger number of samples and items because of the width of the selection of the transitions for measurement.

Further, the isotopologues may be designed so that molecular weights of n types of compounds are different from each other, the isotopologues may contain only plural kinds of the isotope-labeled compounds, the isotopologues may contain n−1 types of labeled compound and one type of not labeled compound. The isotope used for labeling, stable isotopes such as $^2$H (deuterium), $^{13}$C (carbon 13), $^{15}$N (nitrogen 15) and the like are preferably used.

In this embodiment, DAPTAD isotopologues including preferably DAPTAD not labeled with isotope and DAPTAD labeled with stable isotope deuterium ($^2$H) because of its relatively easy to prepare. DAPTAD labeled with $^2$H is preferably different in mass by at least 3 Da from each other in order to minimize the influence of stable isotope of natural origin. In this embodiment, $^2$H$_3$-DAPTAD or $^2$H$_6$-DAPTAD is preferable, such as one or both of the methyl groups of the 4-(4'-dimethylaminophenyl) moiety is labeled with deuterium ($^2$H). In this case, DAPTAD which is not labeled with isotope is denoted as $^2$H$_0$-DAPTAD, and it differs in mass by 3 Da from $^2$H$_3$-DAPTAD, and by 6 Da from $^2$H$_6$-DAPTAD.

DAPTAD may be synthesized based on a known method, that is, by the method described in above S. Ogawa, et al., Rapid Commun. Mass, Spectrom, 25, 2453-2460 (2013). Isotope-labelled DAPTAD, that is, $^2$H$_3$- and $^2$H$_6$-DAPTAD may be synthesized based on the same method.

2.1.3. Derivatization of Vitamin D with DAPTAD

Prior to the derivatization of vitamin D, n types of biological samples such as plasma or serum are first collected and pretreated. For example, acetonitrile containing $^2$H$_6$-25(OH)D$_3$ is added as an internal standard substance to a plasma sample, mixed with a vortex mixer, centrifuged, and the solvent of the supernatant is evaporated from the resultant solution. If necessary, it is preferable to perform protein removal, solid-phase extraction, liquid-liquid extraction, and supported liquid extraction (SLE) using an organic solvent such as methanol.

The residue obtained by the above procedure is derivatized with either DAPTAD, $^2H_3$-DAPTAD or $^2H_6$-DAPTAD. The derivatization step comprising a reaction stopping step of stopping the derivatization reaction by adding a derivatization reaction stopping agent solution containing an alcohol, for example, ethanol. In the reaction stopping step, it is preferable to add a decomposition inhibitor of a derivative to a reaction solution. The decomposition inhibitor exhibits an effect of inhibiting the decomposition of the derivative to be obtained as long as contained in the reaction solution in the reaction stopping step. Therefore, the decomposition inhibitor may be added to the reaction solution before the reaction stopping step or may be added to the reaction stopping agent solution.

In the method for derivatizing according to this embodiment, as the decomposition inhibitor to be used for inhibiting the decomposition of the derivative to be obtained, any compound may be used without particular limitation as long as the compound volatizes easily, and has no effects on separation in LC and ESI ionization in the analysis with the LC/ESI-MS/MS.

As the decomposition inhibitor that may be used in this embodiment, there are given, for example, ammonia and an amine Any one of a primary amine, a secondary amine, and a tertiary amine may be used as the amine Among these, ammonia, trimethylamine, triethylamine, dimethylamine, methylamine, diethylamine, or ethylamine is particularly used in terms of inhibiting the decomposition of the derivative.

Regarding the derivative obtained by the method according to this embodiment, the oxidant remaining after being used for producing the Cookson-type derivatization reagent is decomposed by adding the decomposition inhibitor in the reaction stopping step. With this, the decomposition of the derivative to be obtained is inhibited, with the result that the derivative is obtained in high yield, and moreover, decomposed products and the like generated due to the influence of the remaining oxidant are reduced. By analyzing the derivative obtained by the method according to this embodiment with MS, in particular, LC/MS/MS using electrospray ionization (ESI) (hereinafter sometimes referred to as "LC/ESI-MS/MS"), accurate quantitative analysis can be performed with high sensitivity and selectivity.

In particular, among the vitamin D derivatives, 25(OH) $D_3$S-DAPTAD which is derivatized with 25(OH)$D_3$S may decompose to 25(OH)$D_3$-DAPTAD through desulfoconjugation in some cases. Therefore, when both 25(OH)$D_3$S and 25(OH)$D_3$ are contained in the sample, the ion intensity of 25(OH)$D_3$S-DAPTAD is observed lower than the actual value in case it is decomposed to 25(OH)$D_3$-DAPTAD. Conversely, the ion intensity of 25(OH)$D_3$ is observed higher than the actual value. In this way, in order to suppress the decomposition of 25(OH) $D_3$S-DAPTAD, it is preferable to add a decomposition inhibitor of a derivative in the reaction stopping step, and high sensitive and accurate quantification of 25(OH)$D_3$S-DAPTAD is possible in that case.

In the derivatization of vitamin D, a reagent kit for quantifying vitamin D may be used which including n types of 4-(4'-dimethylaminophenyl)-1,2,4-triazoline-3,5-dione (DAPTAD) isotopologues, a derivatization reaction stopping agent and a decomposition inhibitor of a derivative. In this case, derivitization of vitamin D becomes easy in the quantification of vitamin D. In addition, the kit including n types of DAPTAD isotopologues as a derivatization reagent, it is possible to perform accurate simultaneous quantitative analysis in a small amount in a single measurement. Further, multiple samples (n number) at one measurement is possible. Consequently, it is possible to provide a reagent kit for quantifying vitamin D with improved analysis throughput. Besides, the kit including a derivatization reaction stopping agent and a decomposition inhibitor of a derivative, decomposition of the obtained derivative is suppressed, and more accurate analysis becomes possible.

2.2. Mixing Step

Next, a mixing step of mixing the n types (in the case of 3 types of DAPTAD isotopologs, $^2H_0$-DAPTAD, $^2H_3$-DAPTAD and $^2H_6$-DAPTAD, 3 types.) of samples (Step S12).

2.3. Quantitative Analysis Step

Each of the n types of vitamin D derivatives contained in the mixed sample obtained in the above-mentioned mixing step is subjected to quantitative analysis using the tandem mass spectrometer 100. More specifically, this quantitative analysis step comprises a separation step of separating the mixed sample of derivatization samples by high-performance liquid chromatography, an ionization step of ionizing the separation samples, a first mass separation step of separating the ions generated in the ionization step according to mass and selecting a precursor ion, a cleavage step of cleaving the precursor ion selected in the first mass separation step to generate one or more fragment ions, a second mass separation step of separating the above-mentioned one or more fragment ions generated in the cleavage step according to mass, and an association step of detecting the amount of the one or more fragment ions separated in the second mass separation step and associating the amount of the detected ions with the amount of vitamin D contained in the above-mentioned biological sample.

In the separation step, a solvent of the mixed sample obtained as described above is distilled off and a portion of a sample obtained by dissolving the residue in the mobile phase is loaded by an LC injector (not shown) of the separation unit 10 together with the mobile phase. The mixed sample containing n types of derivatization samples having different masses is separated during the time it passes through the column and elutes from the outlet of the column at different times (Step S14).

Next, MS measurement is carried out as a result of the control unit 48 controlling each of units 10, 20 and 30 of the mass spectrometer 100.

First, the ionization unit 20 ionizes the separated samples (Step S16). Next, the first mass separation unit 32 separates and detects ions generated in the ionization unit 20 according to mass. MS measurement is carried out in this manner. The first mass separation unit 32 outputs information on detection results, namely information on the results of MS measurement, to the processing unit 40.

Next, the precursor ion list generation unit 42 generates a list of precursor ions based on the results of MS measurement.

More specifically, the precursor ion list generation unit 42 acquires MS spectral information from the results of MS measurement. The precursor ion list generation unit 42 then detects peaks appearing in the MS spectra and generates a list of the m/z values of those peaks and the peak intensity (ion intensity) thereof. The resulting list becomes the list of precursor ions.

Next, the precursor ion selection unit 44 selects an ion from the list of precursor ions (Step S18). For example, in the case of selecting 25(OH)D$_3$ as vitamin D and selecting 25(OH)D$_3$-DAPTAD using DAPTAD as reagent, the precursor ion selection unit 44 selects an ion from the list of precursor ions that has a mass-to-charge ratio of 619.5 as the precursor ion of 25(OH)D$_3$-DAPTAD. In addition, in the case of selecting 25(OH)D$_3$S as vitamin D and selecting 25(OH)D$_3$S-DAPTAD using DAPTAD as reagent, the precursor ion selection unit 44 selects an ion from the list of precursor ions that has a mass-to-charge ratio of 699.6±0.5 as the precursor ion of 25(OH)D$_3$S-DAPTAD. In the case of using $^2$H$_3$-DAPTAD or $^2$H$_6$-DAPTAD for the derivatization reagent, the charge-to-mass ratios respectively differ by 3 Da from the above-mentioned values.

Next, the control unit 48 controls each of units 10, 20, 30 and 40 of the mass spectrometer 100 to carry out MS/MS measurement (Step S16). Here, in the case of quantitative analysis using LC/ESI-MS/MS, detection of the amount of fragment ions is carried out preferably using multiple reaction monitoring (MRM) or selected reaction monitoring (SRM) and particularly preferably using SRM. In this case, the derivatized vitamin D is analyzed by suitably selecting a transition. Measurement conditions at that time, such as the column and mobile phase used for LC, are suitably selected corresponding to the analysis target and equipment used.

More specifically, an ion serving as the analysis target is selected from among ions generated in the ionization unit 20 in the first mass separation unit 32, the selected ion is cleaved in the cleavage unit 34 (Step S20), and the fragment ions formed are separated according to mass in the second mass separation unit 36 and subjected to mass spectrometry (Step S22). MS/MS measurement is carried out in this manner. For example, in the case of having selected an ion having a mass-to-charge ratio of 619.5±0.5 for the precursor ion, the mass-to-charge ratio of the fragment ion of 25(OH)D$_3$-DAPTAD is 341.3±0.5. Similarly, in the case of having selected an ion having a mass-to-charge ratio of 699.6±0.5 for the precursor ion, the mass-to-charge ratio of the fragment ion of 25(OH)D$_3$S-DAPTAD is 341.3±0.5. In the case of having used $^2$H$_3$-DAPTAD or $^2$H$_6$-DAPTAD for the derivatization reagent, the charge-to-mass ratios respectively differ by 3 Da from the above-mentioned values.

The second mass separation unit 36 separates and detects one or more fragment ions formed as a result of cleavage according to the mass thereof. Information on detection results, namely information on the results of MS/MS measurement, is output to the processing unit 40. The calculation unit 46 of the processing unit 40 identifies and quantifies vitamin D based on the results of MS/MS measurement (Step S24).

More specifically, the calculation unit 46 generates a peak list by detecting peaks from mass spectral data acquired as a result (MS/MS spectrum) of MS/MS measurement of the selected ion. Each peak (ion) in the acquired peak list is then assigned and vitamin D is identified from the mass-to-charge ratios thereof. Moreover, vitamin D is quantified from ion (peak) intensity, or in other words, the amount of ions.

As has been described above, according to the present embodiment, the use of identical molecules differing only with respect to isotope composition in the form of n types of DAPTAD isotopologues makes it possible to improve selectivity when analyzing by a mass spectrometer as well as simultaneously and quantitatively analyze n number of samples in a single measurement. Consequently, trace amounts of vitamin D contained in n number of samples can be analyzed precisely resulting in improved analysis throughput.

The method for quantifying vitamin D according to this embodiment can also be applied to compounds having s-cis-diene other than vitamin D. There are given, for example, 7-dehydrocholesterol, ergosterol, conjugated linoleic acid, and vitamin A.

Also, the method for quantifying vitamin D according to this embodiment can use isotopologues of Cookson-type derivatization reagent other than DAPTAD. The Cookson-type derivatization reagent other than DAPTAD is not particularly limited, and examples thereof include 4-phenyl-1,2,4-triazoline-3,5-dione (PTAD), 4-[2-(6,7-dimethoxy-4-methyl-3-oxo-3,4-dihydroquinoxalyl)ethyl]-1,2,4-triazoline-3,5-dione (DMEQTAD), 4-(4-nitrophenyl)-1,2,4-triazoline-3,5-dione (NPTAD), and 4-ferrocenylmethyl-1,2,4-triazoline-3,5-dione (FMTAD).

Furthermore, in the present embodiment, examples are shown in which a tandem mass spectrometer (MS/MS) having two mass separation units 32, 36 is used as the mass separation unit 30 of the mass spectrometer 100. However, a mass spectrometer having a high mass resolution that capable of distinguishing clearly the peak of the derivatized sample, analysis can be performed even with one MS.

3. Examples

The present invention is specifically described by way of Experimental Examples and Comparative Examples. However, the present invention is by no means limited to only these Examples. In the description of the following Examples and the like, "%" means "mass %" unless otherwise specified.

3.1. 25(OH)D$_3$ which is Used as Vitamin D

25(OH)D$_3$ was purchased from Wako Pure Chemical Industries (Osaka, Japan). The stock solution of 25(OH)D$_3$ was prepared as a 100 µg/mL solution in ethanol, and its concentration was confirmed by UV spectroscopy using the molar absorptivity (c) of 18200 at 265 nm. Subsequent dilutions were carried out with ethanol to prepare 0.50, 1.0, 2.5, 5.0, 10 and 25 ng/mL solutions. [26,26,26,27,27,27-$^2$H$_6$]-25(OH)D$_3$ [internal standard (IS)] was purchased from IsoSciences (King of Prussia, Pa., USA) and its ethanolic solution (50 ng/mL) was also prepared. DAPTAD was the same as that used in a previous study. All other reagents and solvents were of analytical grade or LC/MS grade.

3.2. Syntheses of DAPTAD Isotopologues

Figure 4:
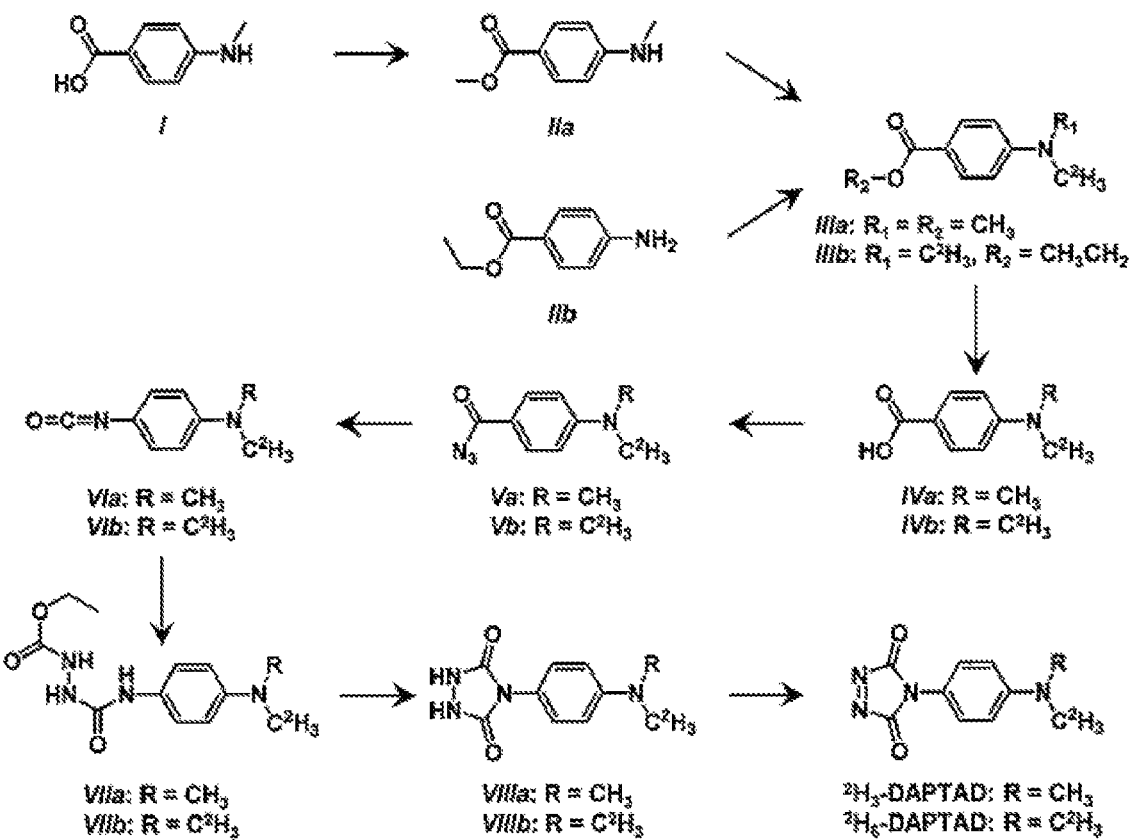
FIG. 4 is a diagram indicating a synthetic scheme of DAPTAD.

Non isotope-labelled DAPTAD was synthesized based on a known method, that is, by the method described in above S. Ogawa, et al., Rapid Commun. Mass, Spectrom, 25, 2453-2460 (2013). Isotope-labelled DAPTAD, that is, $^2$H$_3$- and $^2$H$_6$-DAPTAD were synthesized based on the scheme as described in FIG. 4. All solvents were of the grade that is higher than a commercial best quality product.

First, the intermediates [$^2$H$_3$- and $^2$H$_6$-4-dimethylaminobenzoic acid (IVa and IVb)] for the syntheses of $^2$H$_3$- and $^2$H$_6$-DAPTAD were prepared as described below. The starting materials, 4-methylaminobenzoic acid (I) and ethyl 4-aminobenzoate (IIb) were purchased from Sigma-Aldrich Japan (Tokyo, Japan) and Tokyo Chemical Industry (Tokyo), respectively. Silica gel column chromatography (150×12 mm i.d.) was carried out using a Merck silica-gel 60 (60-200 µm; Darmstadt, Germany). The $^1$H- and $^{13}$C-nuclear magnetic resonance (NMR) spectra of VIIIa and VIIIb in $^2$H$_4$-methanol were recorded using a JEOL JNM-LD400 spectrometer with tetramethylsilane as the internal standard.

A mixture of 4-methylaminobenzoic acid (I, 500 mg, 3.4 mmol) and p-toluenesulfonic acid (50 mg, 0.22 mmol) in methanol (20 mL) was stirred overnight at 60° C. Most of the solvent was evaporated under reduced pressure. The residue was dissolved in ethyl acetate (50 mL), washed with saturated brine (50 mL, 3 times), then dried over MgSO$_4$. After evaporation of the solvent under reduced pressure, the residue was chromatographed on a silica gel column [150× 12 mm i.d., hexane-ethyl acetate (4:1, v/v)] to give methyl 4-methylaminobenzoate (IIa, 172 mg, 1.1 mmol) as a colorless powder.

A mixture of methyl 4-methylaminobenzoate (IIa, 172 mg, 1.1 mmol), $^2$H$_3$-iodomethane (400 μL, 5.7 mmol) and K$_2$CO$_3$ (200 mg, 1.4 mmol) in methanol (2 mL) was stirred overnight at 65° C. The reaction mixture was diluted with ethyl acetate (50 mL), washed with saturated brine (50 mL, 3 times), then dried over MgSO$_4$. After evaporation of the solvent under reduced pressure, the residue was chromatographed on a silica gel column [150×12 mm i.d., hexane-ethyl acetate (4:1, v/v)] to give methyl $^2$H$_3$-4-dimethylaminobenzoate (Ma, 108 mg, 0.59 mmol) as a colorless powder.

A mixture of methyl $^2$H$_3$-4-dimethylaminobenzoate (Ma, 108 mg, 0.59 mmol) and KOH (100 mg, 1.8 mmol) in methanol-water (1:1, v/v, 20 mL) was stirred overnight at 90° C. After evaporation of most of the solvent, the residue was dissolved in water (2 mL), then acidified with acetic acid. Ethyl acetate (50 mL) was added to the mixture, and the organic layer was washed with saturated brine (50 mL, 3 times), then dried over MgSO$_4$. After evaporation of the solvent under reduced pressure, $^2$H$_3$-4-dimethylaminobenzoic acid (IVa, 85 mg, 0.49 mmol) was obtained as a colorless powder. IVa was subjected to the next reaction without purification.

Ethyl $^2$H$_6$-4-dimethylaminobenzoate (Mb) A mixture of ethyl 4-aminobenzoate (IIb, 400 mg, 2.4 mmol), $^2$H$_3$-iodomethane (900 μL, 14.4 mmol) and K$_2$CO$_3$ (400 mg, 2.8 mmol) in ethanol (2 mL) was stirred overnight at 65° C. The reaction mixture was diluted with ethyl acetate (50 mL), washed with saturated brine (50 mL, 3 times), then dried over MgSO$_4$. After evaporation of the solvent under reduced pressure, the residue was chromatographed on a silica gel column [150×12 mm i.d., hexane-ethyl acetate (7:3, v/v)] to give ethyl $^2$H$_6$-4-dimethylaminobenzoate (Mb, 225 mg, 1.2 mmol) as a colorless powder.

$^2$H$_6$-4-Dimethylaminobenzoic acid (IVb) A mixture of ethyl $^2$H$_6$-4-dimethylaminobenzoate (Mb, 225 mg, 1.2 mmol) and KOH (100 mg, 1.8 mmol) dissolved in methanol-water (1:1, v/v, 20 mL) was stirred overnight at 90° C. After evaporation of most of the solvent, the residue was dissolved in water (2 mL), then acidified with acetic acid. Ethyl acetate (50 mL) was added to the mixture, and the organic layer was washed with saturated brine (50 mL, 3 times), then dried over MgSO$_4$. After evaporation of the solvent under reduced pressure, $^2$H$_6$-4-dimethylaminobenzoic acid (IVb, 160 mg, 0.93 mmol) was obtained as a colorless powder. IVb was subjected to the next reaction without purification.

The conversion of the carboxylic acids (IVa and IVb) to $^2$H$_3$- and $^2$H$_6$-DAPTAD, respectively, was carried out according to the known method, that is, the method described in above S. Ogawa, et al., Rapid Commun. Mass, Spectrom, 25, 2453-2460 (2013). Briefly, the carboxylic acid (IVa or IVb) was treated with diphenylphosphoryl azide to produce the carbonyl azide (Va or Vb), which was converted into the isocyanate (VIa or VIb) by Curtius rearrangement. The isocyanate (VIa or VIb) was treated with ethyl hydrazinecarboxylate to produce the ethoxycarbonylsemicarbazide (VIIa or VIIb). The semicarbazide (VIIa or VIIb) was cyclized by alkaline treatment to produce the triazolidine (VIIIa or VIIIb), which was then oxidized with iodobenzene diacetate in ethyl acetate to form either DAPTAD isotopologue as a red solution.

3.3. DAPTAD-Derivatization of V.D.

The samples prepared as described below were dried, then dissolved in the DAPTAD, $^2$H$_3$-DAPTAD or $^2$H$_6$-DAPTAD ethyl acetate solution [10 μg in ethyl acetate (50 μL)] obtained in the section 3.2. The mixture was stored at room temperature for 1 h, then ethanol (20 μL) was added to the mixture to terminate the reaction.

3.4. Analysis Conditions of LC/ESI-MS/MS 3.4.1. Device for Use

A Waters (trademark) Quattro Premier XE triple quadrupole mass spectrometer (Nihon Waters K.K.) connected to an LC-e2695 chromatograph (Nihon Waters K.K.) was used as LC/MS/MS, and ESI was used for the ionization method. Analysis was performed under the following analysis conditions.

3.4.2. Analysis Conditions

Column: YMC-Pack Pro C18 RS (3 μm, 150×2.0 mm i.d.)

Column temperature: 40° C.

Mobile phase: 0.05% formic acid-containing methanol-10 mM ammonium formate (4:1, v/v)

Flow rate: 0.2 ml/min

Ionization mode: ESI (+)

Capillary voltage: 3.3 kV

Cone voltage: 40 V [25(OH)D$_3$-DAPTAD], 35 V [25 (OHD)$_3$S-DAPTAD], or 30 V [25(OH)D$_3$-DAPTAD]

CE (Collision energy): 25 eV

Source temperature: 120° C.

Desolvation temperature: 400° C.

Desolvation gas (N$_2$) flow rate: 800 L/h

Cone gas (N$_2$) flow rate: 50 L/h

Collision gas (Ar) flow rate: 0.19 ml/min

The selected reaction monitoring (SRM) transitions (precursor and product ions) are as described in Table 1.

For analysis of data, QuanLynx that was an automatic processing system in Waters (trademark) MassLynx 4.1 software was used.

TABLE 1

| | SRM transitions | | |
|---|---|---|---|
| derivatization reagent | 25(OH)D$_3$ | $^2$H$_6$-25(OH)D$_3$-DAPTA | 25(OH)D$_3$S |
| DAPTAD | m/z 619.5 → 341.3 | m/z 625.5 → 341.3 | m/z 699.5 → 341.3 |
| $^2$H$_3$-DAPTAD | m/z 622.5 → 344.3 | m/z 628.5 → 344.3 | m/z 702.5 → 344.3 |
| $^2$H$_6$-DAPTAD | m/z 625.5 → 347.3 | m/z 631.5 → 347.3 | m/z 705.5 → 347.3 |

3.5. Plasma Samples

The development and validation of the method according to one embodiment of the present invention were carried out using a FFP-LR Nisseki frozen plasma obtained from the Japan Red Cross Service (Tokyo), which is described as the adult plasma in this study. The plasma samples from Japanese infants were also used. Blood was collected from their dorsal hand vein within 60 days after birth at the Shizuoka Saiseikai General Hospital (Shizuoka, Japan). Written informed consent was obtained from their parents. The experimental procedures were approved by the Ethics Committee of the Tokyo University of Science.

3.6. Pretreatment Procedure

The plasma (5.0 μL) was added to acetonitrile (100 μL) containing IS (50 pg) and vortex-mixed for 30 s, then centrifuged at 1000 g for 10 min. The supernatant was transferred to another test tube and the solvent was evaporated under an $N_2$ gas stream. The residue was subjected to derivatization with either DAPTAD, $^2H_3$-DAPTAD or $^2H_6$-DAPTAD. Three different samples derivatized with the different DAPTAD isotopologue were mixed and the solvent was evaporated. The residue was dissolved in the mobile phases (60 μL), 15 μL of which was subjected to LC/ESI-MS/MS.

3.7. Preparation of Surrogate Matrix [25(OH)$D_3$-Free Plasma Extract]

The plasma (1.0 mL) was added to acetonitrile (9.0 mL) and vortex-mixed for 30 s, then centrifuged at 1000 g for 10 min. The supernatant was transferred to another test tube and stirred with charcoal (1.0 g, NoritR, Nacalai Tesque, Kyoto) for 15 h. After centrifugation at 2000 g for 10 min to remove the charcoal, the supernatant was diluted with acetonitrile in a measuring flask to 10 mL total and used as the surrogate matrix [25(OH)$D_3$-free plasma extract]. Fifty microliters of the surrogate matrix contain the components derived from 5 μL of plasma.

3.8. Calibration Curves

IS (50 pg) and a graduated amount of 25(OH)$D_3$ (5.0, 10, 25, 50, 100 or 250 pg; corresponding to 1.0, 2.0, 5.0, 10, 20 or 50 ng/mL, respectively) were added to the surrogate matrix (50 μL, corresponding to 5 μL plasma). After evaporation of the solvent, the residue was derivatized as described in Section 2.4. The 3 samples, which contained the same amounts of 25(OH)$D_3$ but were derivatized with the different DAPTAD isotopologues, were mixed and the solvent was evaporated. The residue was dissolved in the mobile phase and subjected to LC/ESI-MS/MS. The peak area ratios [derivatized 25(OH)$D_3$/IS] (y) were plotted versus the concentration of 25(OH)$D_3$ (ng/mL plasma) (x), and the obtained regression lines were used as the calibration curves.

3.9. Equality of DAPTAD Isotopologues in 25(OH)$D_3$ Quantification

Three aliquots of the same plasma (5.0 μL each) were separately added to acetonitrile (100 μL) containing IS (50 pg), pretreated, then derivatized with the different DAPTAD isotopologues. The resulting 3 samples were mixed and the solvent was evaporated. The residue was dissolved in the mobile phase and subjected to LC/ESI-MS/MS. The measured 25(OH)$D_3$ concentrations of the DAPTAD-, $^2H_3$-DAPTAD- or $^2H_6$-DAPTAD-derivatized samples were compared. This test was carried out for 10 different plasma samples (5 adult and 5 infant plasma samples).

3.10. Assay Precision and Accuracy

The assay precision was examined using 2 batches consisting of 3 different plasma samples; batch A (plasma A-1, A-2 and A-3) and batch B (plasma B-1, B-2 and B-3). DAPTAD was used for the analyses of plasma A-1 and B-1, $^2H_3$-DAPTAD was used for the plasma A-2 and B-2, $^2H_3$-DAPTAD was used for the plasma A-3 and B-3. The intra-(n=5) and inter-assay (n=5) precisions were assessed by the repeated measurement of the samples on one day and over five days, respectively. The precision was determined as the relative standard deviation (RSD, %).

The assay accuracy was examined using batches A and B. The plasma samples (5.0 μL) were added to acetonitrile (100 μL) containing IS (50 pg) and 25(OH)$D_3$ (12.5, 25, 50 or 100 pg; corresponding to 2.5, 5.0, 10 or 20 ng/mL)(spiked sample), pretreated, then derivatized with either DAPTAD, $^2H_3$-DAPTAD or $^2H_6$-DAPTAD. The assay accuracy (analytical recovery) was defined as $F/(F_0+X)\times100(\%)$, where F is the concentration of 25(OH)$D_3$ in the spiked sample, $F_0$ is the concentration of 25(OH)$D_3$ determined in the inter-assay precision test and X is the spiked concentration.

3.11. Matrix Effects

The matrix effects were examined in a post-extraction addition experiment. Standard samples of the DAPTAD-, $^2H_3$-DAPTAD- or $^2H_6$-DAPTAD-derivatized 25(OH)$D_3$ (50 pg/60 μL, n=5) and matrix samples, which had been prepared by adding the extracts from 15 μL of the plasma samples to the standard DAPTAD-, $^2H_3$-DAPTAD- or $^2H_6$-DAPTAD-derivatized 25(OH)$D_3$ (50 pg/60 μL, n=5), were analyzed.

3.12. Standard Method for the Determination of Plasma 25(OH)$D_3$

The plasma (5.0 μL) was pretreated in the same way as described above. The pretreated sample was derivatized with DAPTAD, then subjected to LC/ESI-MS/MS. Thus, in the "standard method", one sample was analyzed during a single LC/ESI-MS/MS run. The standard method also employed the DAPTAD-derivatization to avoid overestimation of the 25(OH)$D_3$ concentrations by 3-epi-25(OH)$D_3$.

3.13. Results and Discussion

To minimize the negative effects of naturally-occurring stable isotopes on the simultaneous quantification of 3 different samples, we designed the DAPTAD isotopologues which differ in mass by at least 3 Da from one another. The DAPTAD isotopologues were synthesized according to the previously reported method. The DAPTAD isotopologues solutions were prepared by the oxidation of the respective triazolidine precursors in ethyl acetate in advance of the derivatization and stored as described in Section 3.2. When stored at −18° C., the solutions could be used for the derivatization within the next 2 months.

The isotopic purities of $^2H_3$- and $^2H_6$-DAPTAD were determined by LC/ESI-MS (selected ion monitoring) after they were reacted with 25(OH)$D_3$. The DAPTAD isotopologues reacted with 25(OH)$D_3$ at room temperature for 1 h; our previous study demonstrated that the DAPTAD-derivatization quantitatively proceeded under this reaction condition.

By monitoring the respective protonated molecules ([M+H])$^+$ of the $^2H_3$-, $^2H_2$-, $^2H_1$- and $^2H_0$-forms (m/z 622.5, 621.5, 620.5 and 619.5, respectively), the isotopic purity of $^2H_3$-DAPTAD was found to be greater than 99.0% (the content of $^2H_5$-form was 0.98% and $^2H_1$- and $^2H_0$-forms were not detected at all). The isotopic purity of $^2H_6$-DAPTAD (monitoring ion, m/z 625.5) was found to be ca. 98.5% in a similar way (the content of 5-form was 1.50% and $H_4$-, $H_3$-, $H_2$-, $H_1$- and $H_0$-forms were not detected at all). Thus, the DAPTAD isotopologues synthesized in this study had satisfactory isotopic purities.

Figure 5:
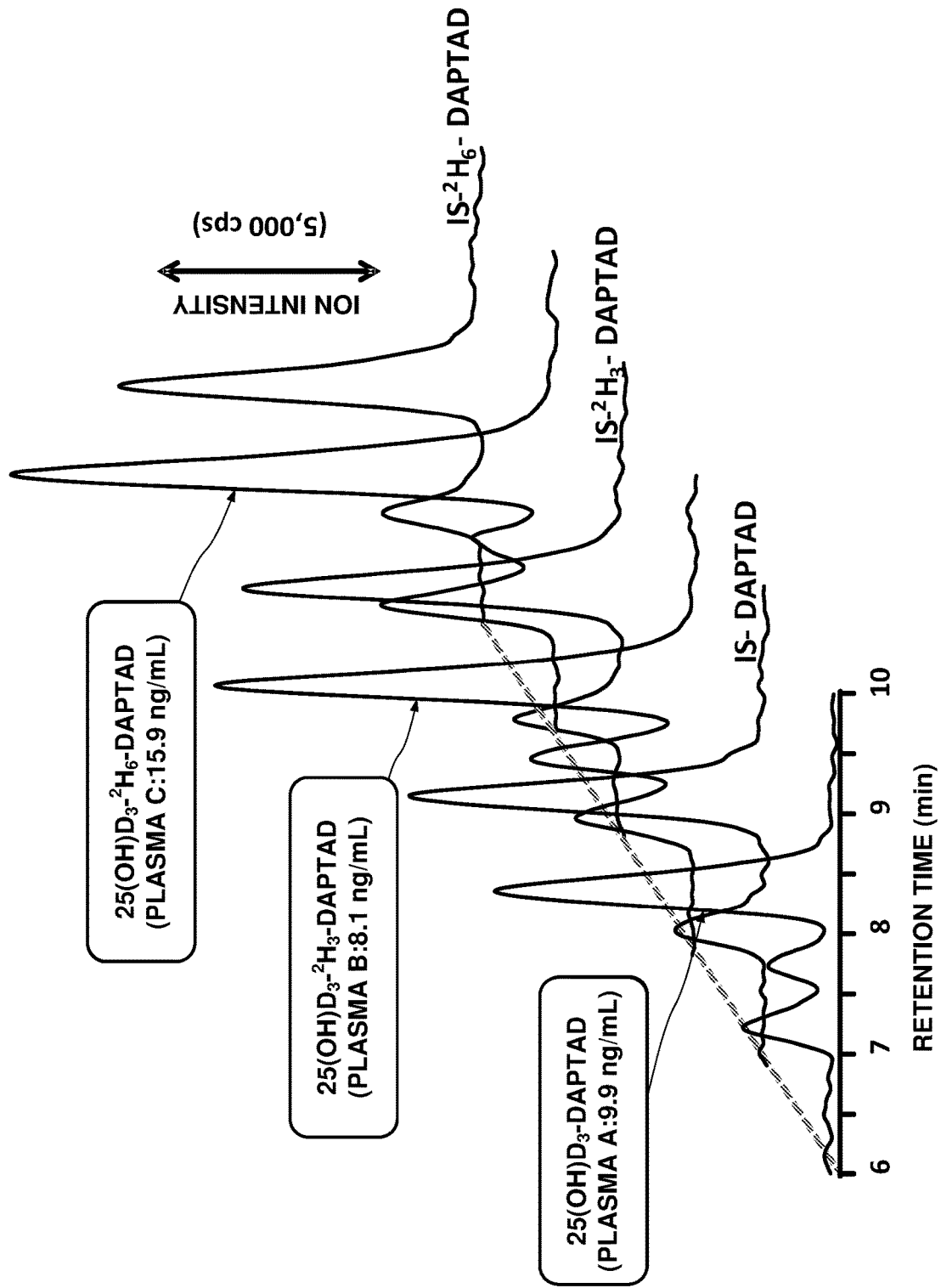
FIG. 5 is a mass chromatogram indicating simultaneous quantification of 3 different samples.

As shown in FIG. 5, the ESI-MS and -MS/MS behaviors of 25(OH)$D_3$-DAPTAD, -$^2H_3$-DAPTAD and -$^2H_6$-DAPTAD were similar; all the derivatives provided [M+H]$^+$ at m/z 619.5, 622.5 and 625.5, respectively, as the base peaks in the positive ESI-MS, and the collision-induced dissociation of [M+H]$^+$ gave the characteristic A-ring fragment ions at m/z 341.3, 344.3 and 347.3, respectively, which were derived from the cleavage of the C-6.7 bond of the vitamin D skeleton. The derivatized IS, $^2H_6$-25(OH)$D_3$-

DAPTAD, -$^2$H$_3$-DAPTAD or -$^2$H$_6$-DAPTAD showed similar fragmentation patterns (m/z 625.5→341.3, 628.5→344.3 or 631.5→347.3, respectively). Thus, the fragmentation patterns showed no overlap between individual ions and therefore, no interference between the derivatives. The SRM transitions described in Table 1 were used for the quantification of 25(OH)D$_3$ in the plasma. The limits of detection were 0.25 fmol in Table 1 (signal-to-noise ratio of 5) for all the derivatives.

As already described, to minimize the negative effects of the naturally-occurring stable isotopes on the quantification, the DAPTAD isotopologues were designed based on the concept that one isotopologue differs in mass by at least 3 Da from another. To verify this point, the DAPTAD- and $^2$H$_3$-DAPTAD-derivatives were subjected to LC/ESI-MS/MS and the isotopic ion peaks at m/z 344.3 and 347.3 (corresponding to the monoisotopic mass of [M+H]$^+$ plus 3 Da, respectively) were monitored. As a consequence, their intensities were negligibly low (below 0.6% intensity of monoisotopic mass of [M+H]$^+$ of $^2$H$_3$-DAPTAD- or $^2$H$_6$-DAPTAD-derivative); these results demonstrated that the isotopic peaks of the DAPTAD- and $^2$H$_3$-DAPTAD-derivatives, which were derived from the naturally-occurring stable isotopes, had negligible effects on the quantification of the $^2$H$_3$-DAPTAD- and $^2$H$_6$-DAPTAD-derivatives, respectively.

As shown in FIG. 5, the $^2$H$_3$-DAPTAD-derivatives always eluted slightly earlier (ca. 0.1 min) than the DAPTAD-derivatives under the LC conditions. The $^2$H$_6$-DAPTAD-derivatives also eluted ca. 0.1 min earlier than the $^2$H$_3$-DAPTAD-derivatives. Thus, the isotope effect was observed, because the $^2$H-coded isotopologues generally have weaker hydrophobic interactions with the stationary phase of reversed-phase LC than their H-coded counterparts. However, the isotope effect had a very minimal detrimental effect on the quantitative analysis of 25(OH)D$_3$ in the plasma. As shown in FIG. 3, the derivatives of 25(OH)D$_3$ with the DAPTAD isotopologues consisted of the 6R- and 6S-isomers and the 6S-isomers were the major products. In this study, the 6S-isomers were used for the plasma 25(OH)D$_3$ quantification.

3.14. Calibration Curves

For bioanalytical methods, an unaltered native matrix should be used to construct a calibration curve when available. However, 25(OH)D$_3$ is an endogenous compound and the 25(OH)D$_3$-free plasma was not available. Although the saline containing 7% human serum albumin could be also used as the matrix for the construction of the calibration curves, we think that the surrogate matrix prepared from the plasma is the better 25(OH)D$_3$-free matrix similar to the native matrix.

Figure 6:
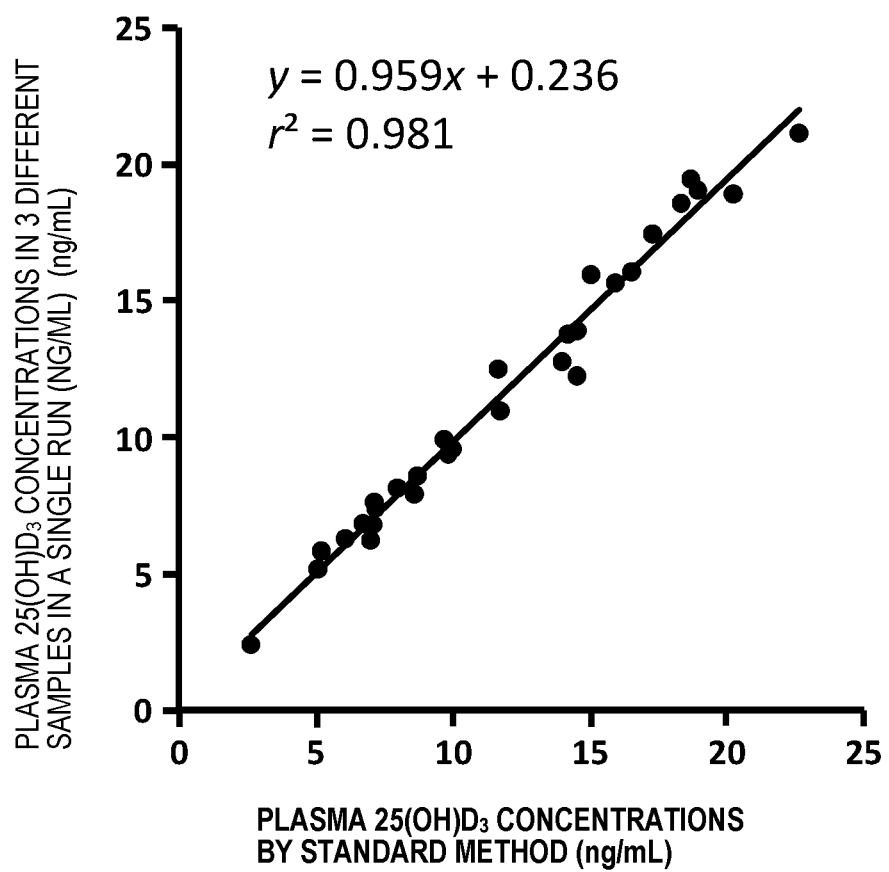
FIG. 6 is a correlations between plasma $25(OH)D_3$ concentrations by the developed method (DAPTAD isotopologue derivatization method) and those by the standard method.

As described in FIG. 6 and Table 2, a satisfactory linearity with determination coefficients (r$^2$) greater than 0.998 was obtained for either DAPTAD isotopolugue. The reproducible calibration curves were obtained as demonstrated that the RSD of the slopes of 5 curves constructed using 5 different surrogate matrices were very small; 0.76% [slope 0.01966±0.00015 (mean±SD)] for DAPTAD-derivative, 0.86% (0.01985±0.00017) for $^2$H$_3$-DAPTAD-derivative and 1.11% for $^2$H$_6$-DAPTAD-derivative (0.01983±0.00022). There was no significant difference in the slopes of the respective calibration curves using either isotopologue. The y-intercepts of the calibration curves were also close to zero (0.00275-0.00614).

TABLE 2

| derivatization reagent | slope (mean ± SD) | y-intercept | r$^2$ |
|---|---|---|---|
| DAPTAD | 0.01966 ± 0.00015, 0.75 | 0.00275 | >0.999 |
| $^2$H$_3$-DAPTAD | 0.01985 ± 0.00017, 0.84 | 0.00544 | >0.998 |
| $^2$H$_6$-DAPTAD | 0.01983 ± 0.00022, 1.12 | 0.00614 | >0.998 |

3.15. Equality of DAPTAD Isotopologues in 25(OH)D$_3$ Quantification

Three aliquots of the same plasma were simultaneously analyzed after the derivatization with the different DAPTAD isotopologues, and the measured values [25(OH)D$_3$ concentrations] were compared. As is obvious from Table 3, whichever isotopologue was used, similar values were obtained from the same plasma samples; the RSD of the measured values did not exceed 4.2%. Thus, every DAPTAD isotopologue can work in the same manner for the quantification of 25(OH)D$_3$ in the plasma.

TABLE 3

Equality of DAPTAD isotopologues in 25(OH)D$_3$ quantification

| | Measured concentration (ng/mL) | | | Mean ± SD | |
|---|---|---|---|---|---|
| | DAPTAD | $^2$H$_3$-DAPTAD | $^2$H$_6$-DAPTAD | (ng/mL) | RSD (%) |
| Adult plasma | | | | | |
| Plasma 1 | 19.26 | 19.23 | 18.70 | 19.06 ± 0.32 | 1.7 |
| Plasma 2 | 16.33 | 15.47 | 16.08 | 15.96 ± 0.44 | 2.8 |
| Plasma 3 | 13.67 | 14.48 | 14.78 | 14.31 ± 0.57 | 4.0 |
| Plasma 4 | 14.30 | 15.25 | 14.78 | 14.78 ± 0.48 | 3.2 |
| Plasma 5 | 18.40 | 17.81 | 17.27 | 17.83 ± 0.57 | 3.2 |
| Infant plasma | | | | | |
| Plasma 6 | 2.65 | 2.80 | 2.73 | 2.73 ± 0.08 | 2.9 |
| Plasma 7 | 5.27 | 5.24 | 5.29 | 5.27 ± 0.03 | 0.6 |
| Plasma 8 | 6.57 | 6.58 | 6.59 | 6.58 ± 0.01 | 0.2 |
| Plasma 9 | 8.42 | 8.05 | 7.93 | 8.13 ± 0.26 | 3.2 |
| Plasma 10 | 1.51 | 1.59 | 1.64 | 1.58 ± 0.07 | 4.4 |

3.16. Assay Precision and Accuracy

For the simultaneous analysis of 3 different plasma samples using the triplex DAPTAD isotopologues, the intra-assay (n=5) RSDs did not exceed 5.9%, as shown in Table 4. Satisfactory inter-assay (n=5) RSDs (≤5.5%) were also obtained. The analytical recovery ranged from 98.7 to 102.2%, which demonstrated that the proposed method is accurate.

derivatization, the assay sensitivity was increased approximately 30-fold and the limit of quantification of the method was 1.0 ng/mL when a 5.0 µL plasma was used; thus, the

TABLE 4

Assay precision and accuracy

|  | Batch A | | | Batch B | | |
| --- | --- | --- | --- | --- | --- | --- |
|  | Plasma A-1 (DAPTAD) | Plasma A-2 ($^2H_3$-DAPTAD) | Plasma A-3 ($^2H_6$-DAPTAD) | Plasma B-1 (DAPTAD) | Plasma B-2 ($^2H_3$-DAPTAD) | Plasma B-3 ($^2H_6$-DAPTAD) |
| Intact sample (intra-assay, n = 5) | | | | | | |
| Measured$^a$ (ng/mL) | 18.35 ± 0.53 | 8.62 ± 0.17 | 2.47 ± 0.07 | 4.74 ± 0.28 | 15.53 ± 0.67 | 19.78 ± 0.53 |
| Precision (RSD, %) | 2.9 | 2.0 | 2.8 | 5.9 | 4.3 | 2.7 |
| Intact sample, (inter-assay; n = 5) | | | | | | |
| Measured$^a$ (ng/mL) | 18.93 ± 0.67 | 9.15 ± 0.38 | 2.56 ± 0.14 | 4.59 ± 0.21 | 15.58 ± 0.57 | 19.66 ± 0.72 |
| Precision (RSD, %) | 3.5 | 4.2 | 5.5 | 4.6 | 3.7 | 3.7 |
| Spiked sample (n = 2) | | | | | | |
| Spiked (ng/mL) | +10.0 | +5.0 | +2.5 | +5.0 | +10.0 | +20.0 |
| Measured$^a$ (ng/mL) | 28.58 | 13.97 | 5.17 | 9.53 | 25.89 | 40.51 |
| Accuracy (%) | 98.8 | 98.7 | 102.2 | 99.4 | 101.2 | 102.1 |

$^a$Mean or mean ± SD.

3.17. Matrix Effects

Because 3 plasma extracts were combined for the simultaneous measurements of 3 different samples, the multiplied matrix effects (ion suppression) were of concern. However, the results of the post-extraction addition experiment demonstrated that the matrix effects were not very significant; the responses of the matrix samples were 89.7±5.9, 86.8±7.7 and 90.9±11.9% (mean±SD, n=5) of those of the standard samples for the DAPTAD-, $^2H_3$-DAPTAD- and $^2H_6$-DAPTAD derivatives, respectively.

3.18. Applicability of the Newly Developed Method

To demonstrate the applicability of the newly developed method, 16 batches (total 48 plasma samples) were analyzed based on the method using the triplex DAPTAD isotopologues. A batch consisted of 3 different plasma samples, which were collected from 23 adults and 25 infants. Only 5.0 µL of plasma was used for the 25(OH)D$_3$ measurement due to the high response of the DAPTAD derivative to ESI-MS/MS. The pretreatment procedure was also very simple; only deproteinization was needed prior to the derivatization.

Figure 7:
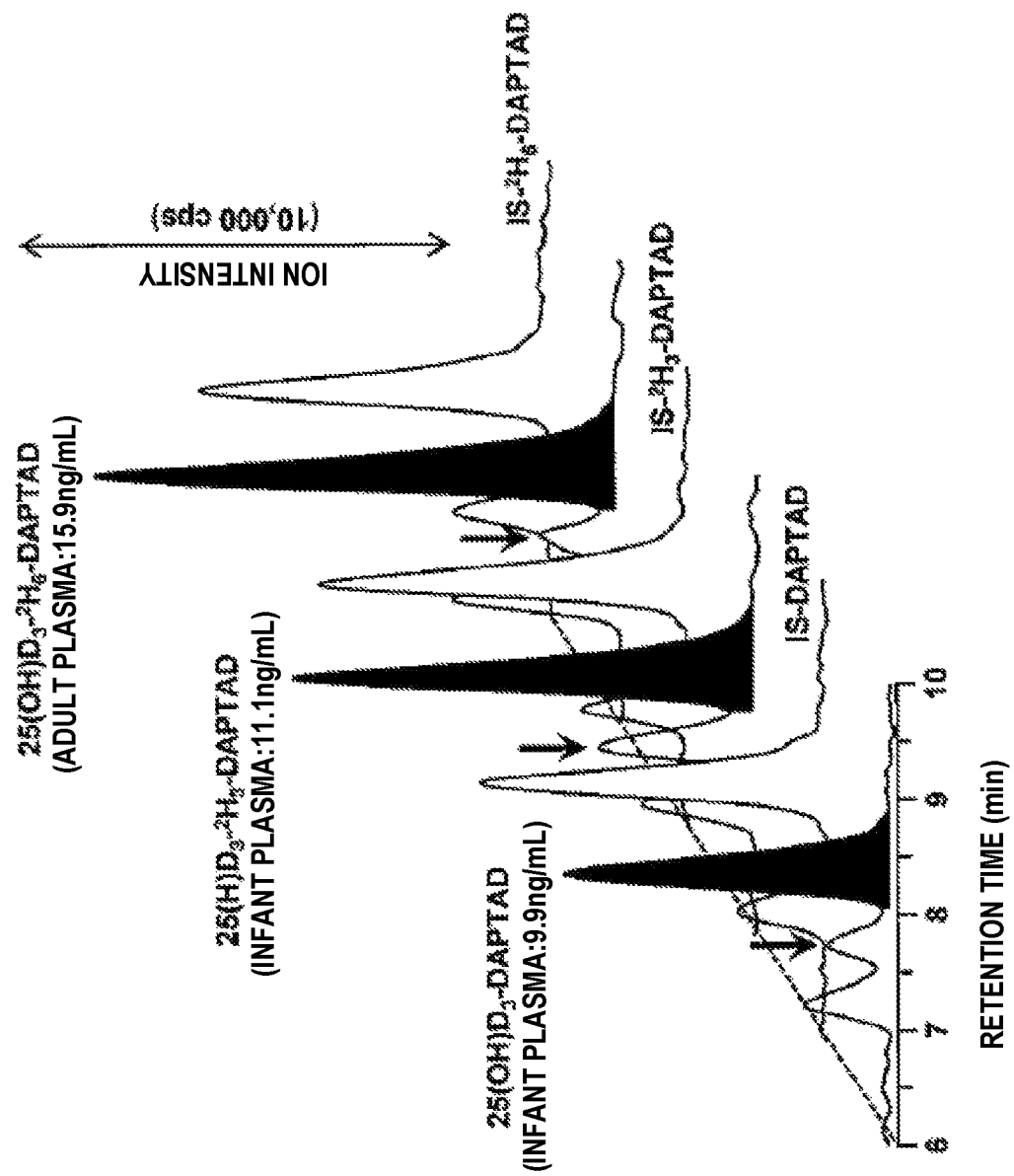
FIG. 7 is a mass chromatogram indicating simultaneous quantification of 3 different plasma samples.

The chromatograms obtained from a batch, which consisted of 1 adult and 2 infant samples, are shown in FIG. 7, in which the peaks corresponding to the derivatized 25(OH)D$_3$ ($t_R$ 8.3 min: DAPTAD-derivative, $t_R$ 8.2 min: $^2H_3$-DAPTAD-derivative and $t_R$ 8.1 min: $^2H_6$-DAPTAD-derivative) and IS ($t_R$ 8.2 min: DAPTAD-derivative, $t_R$ 8.1 min: $^2H_3$-DAPTAD-derivative and $t_R$ 8.0 min: $^2H_6$-DAPTAD-derivative) were clearly observed without interference from 3-epi-25(OH)D$_3$. Thus, the new method was comparable to our previous method in its capability of separating the interfering metabolite.

Figure 8:
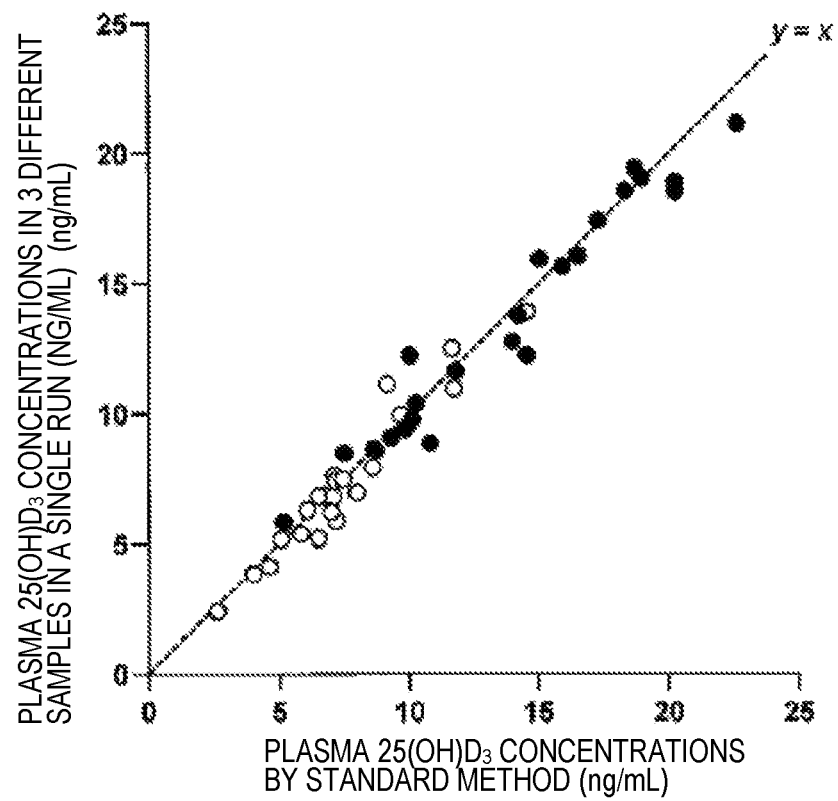
FIG. 8 is a correlations between plasma $25(OH)D_3$ concentrations by the developed method (DAPTAD isotopologue derivatization method) and those by the standard method.

The batch-measured concentrations using the triplex DAPTAD isotopologues [10.4±4.8 ng/mL (mean±SD), 2.4-21.1 ng/mL (range)] well agreed with those by the standard method (FIG. 8), in which one sample was analyzed during a single LC/ESI-MS/MS run (10.6±4.9 ng/mL, 2.6-22.7 ng/mL). A good correlation was observed between the measured values of the two methods (y=0.9555x+0.2442, r$^2$=0.968). The plasma 25(OH)D$_3$ concentrations of infants (2.4-13.9 ng/mL, open circle) were significantly lower than those of adults (5.8-21.1 ng/mL, closed circle). By the newly developed method was capable of analyzing low 25(OH)D$_3$ content samples like the infant plasma. The isotopologue derivatization method could determine the plasma 25(OH)D$_3$ concentration of 3 different samples within a single LC/ESI-MS/MS run, which reduced the analysis time to ⅓ (from 540 min to 170 min for 48 samples).

3.19. Simultaneous Quantification of 25(OH)D$_3$ and 25(OH)D$_3$S in Plasma

Simultaneous quantification of 25(OH)D$_3$ and 25(OH)D$_3$S in plasma was performed. In this example, 20 µL of plasma sample was used as a sample. Prior to derivatization, solid phase extraction was carried out with deproteinization and Oasis (registered trademark) HLB (product name, manufactured by Nippon Waters Co., Ltd.) as pretreatment. $^2H_3$-25(OH)D$_3$ and $^2H_6$-25(OH)D$_3$S were used as internal standards.

Figure 9:
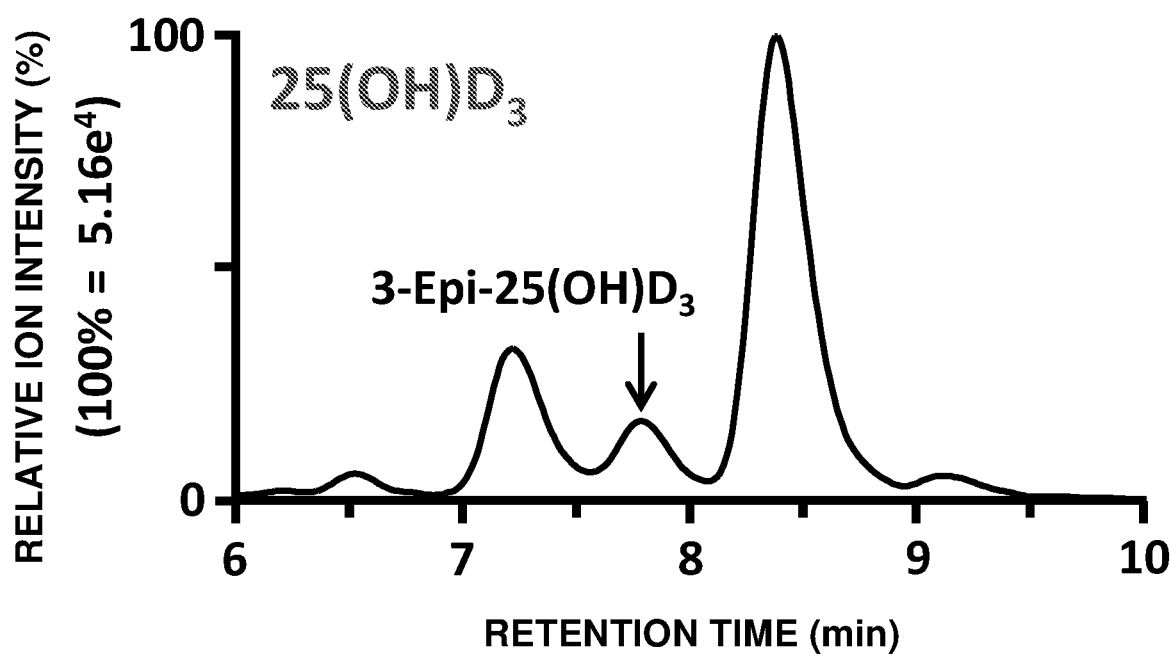
FIG. 9 is a mass chromatogram of $25(OH)D_3$ indicating simultaneous quantification of $25(OH)D_3$ and $25(OH)D_3S$ in neonatal plasma.
Figure 10:
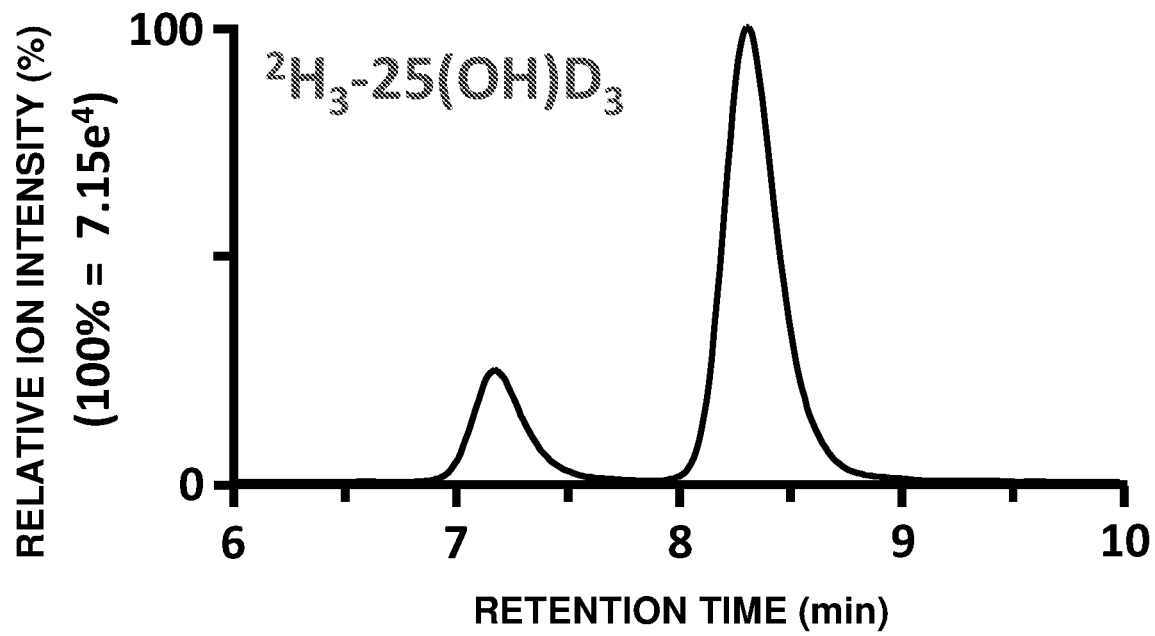
FIG. 10 is a mass chromatogram of $^2H_3$-$25(OH)D_3$ indicating simultaneous quantification of $25(OH)D_3$ and $25(OH)D_3S$ in neonatal plasma.
Figure 11:
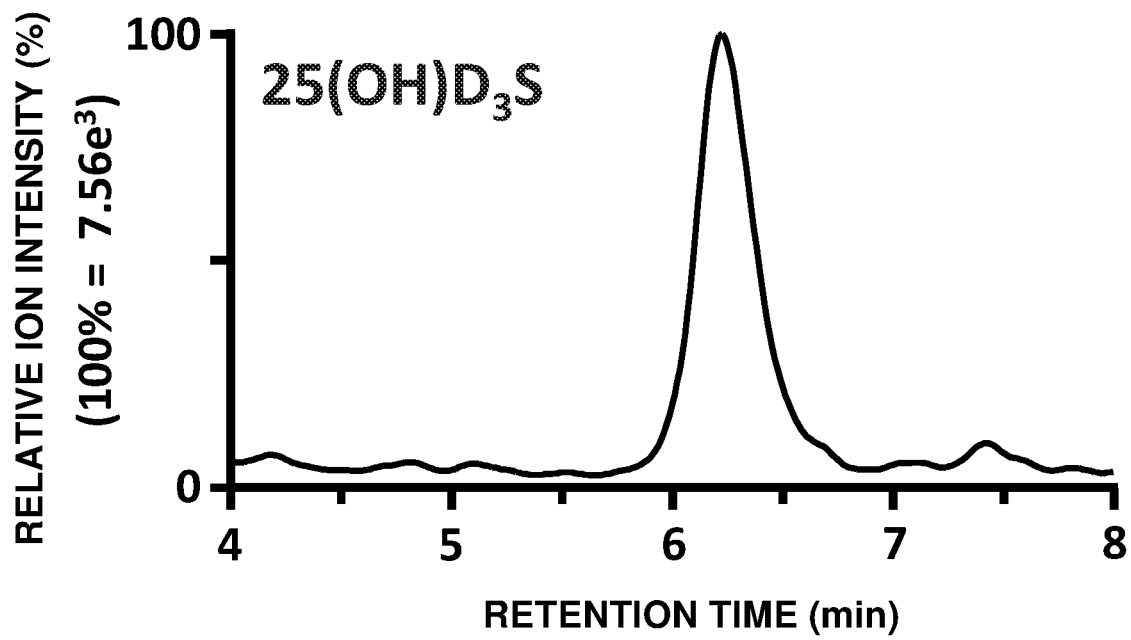
FIG. 11 is a mass chromatogram of $25(OH)$ $D_3S$ indicating simultaneous quantification of $25(OH)D_3$ and $25(OH)D_3S$ in neonatal plasma.
Figure 12:
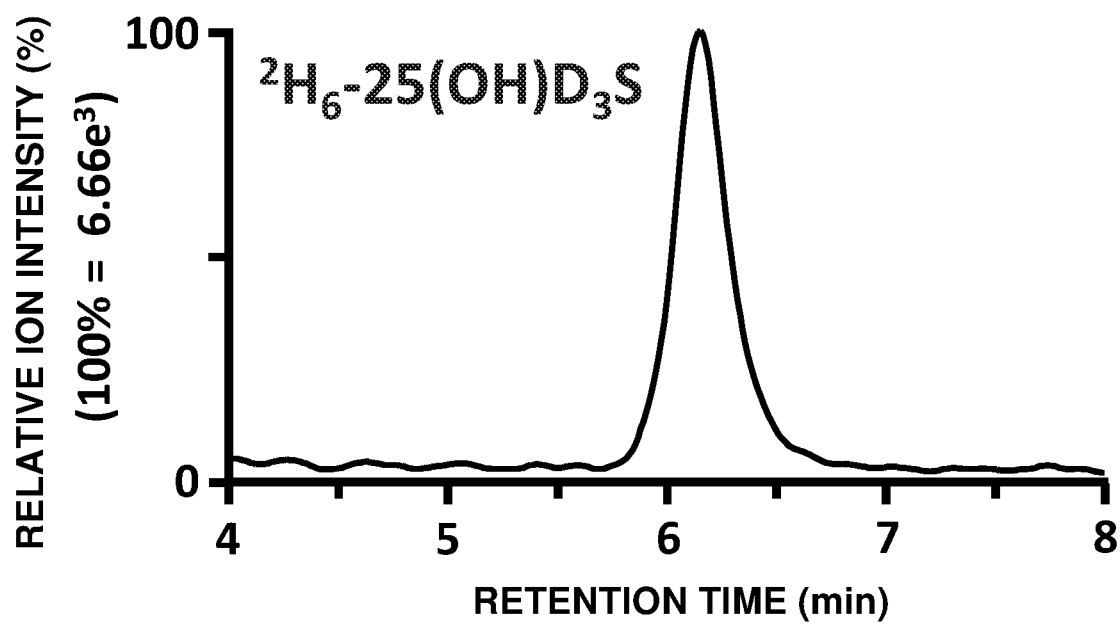
FIG. 12 is a mass chromatogram of $^2H_6$-$25(OH)$ $D_3S$ indicating simultaneous quantification of $25(OH)D_3$ and $25(OH)D_3S$ in neonatal plasma.
Figure 13:
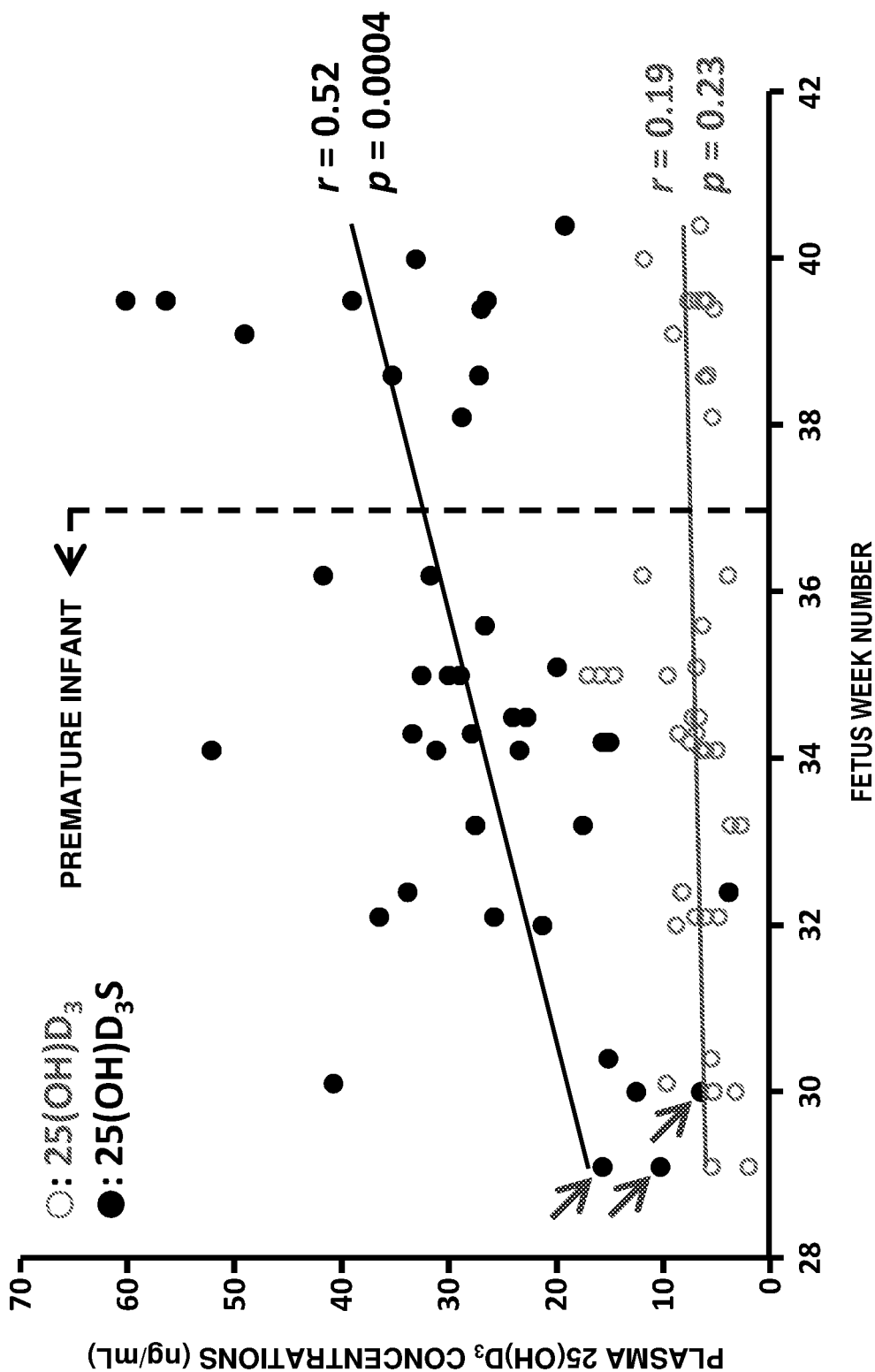
FIG. 13 is a diagram indicating the correlation with the gestational week number, and the concentration of $25(OH)D_3$ and $25(OH)D_3S$ in neonatal plasma.

The obtained results are shown in FIG. 9 to FIG. 12. As shown in FIG. 9 and FIG. 10, the derivatized 25(OH)D$_3$ and IS were clearly observed without interfering with 3-epi-25(OH)D$_3$. Similarly, as shown in FIG. 11 and FIG. 12, derivatized 25(OH)D$_3$ and IS were clearly observed without interfering with each other at retention times different from 25(OH)D$_3$ and IS. In addition, as shown in FIG. 13, the concentration of 25(OH) D$_3$S in neonatal plasma tended to correlate with the gestational week number, and the concentration is tended to be lower in preterm infants.

3.20. Effect of Using the Decomposition Inhibitor

Description is given of the effect of adding triethylamine as the decomposition inhibitor of a derivative in the reaction stopping step of derivatizing 25(OH)D$_3$ with DAPTAD as shown in FIG. 14 to FIG. 17.

Figure 14:
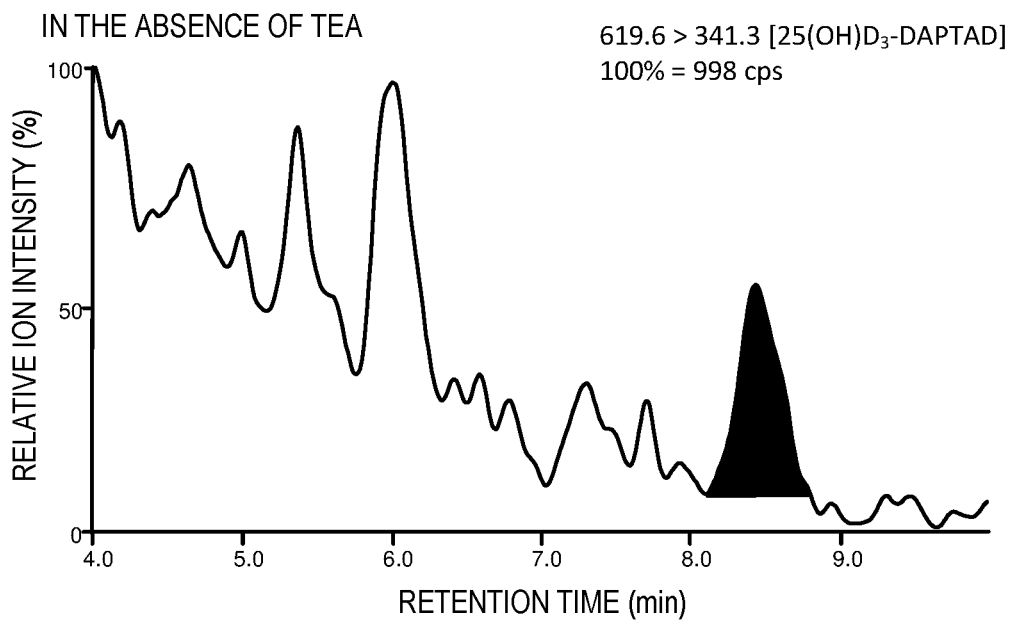
FIG. 14 is a mass chromatogram of $25(OH)D_3$-DAPTAD in the absence of triethylamine.
Figure 15:
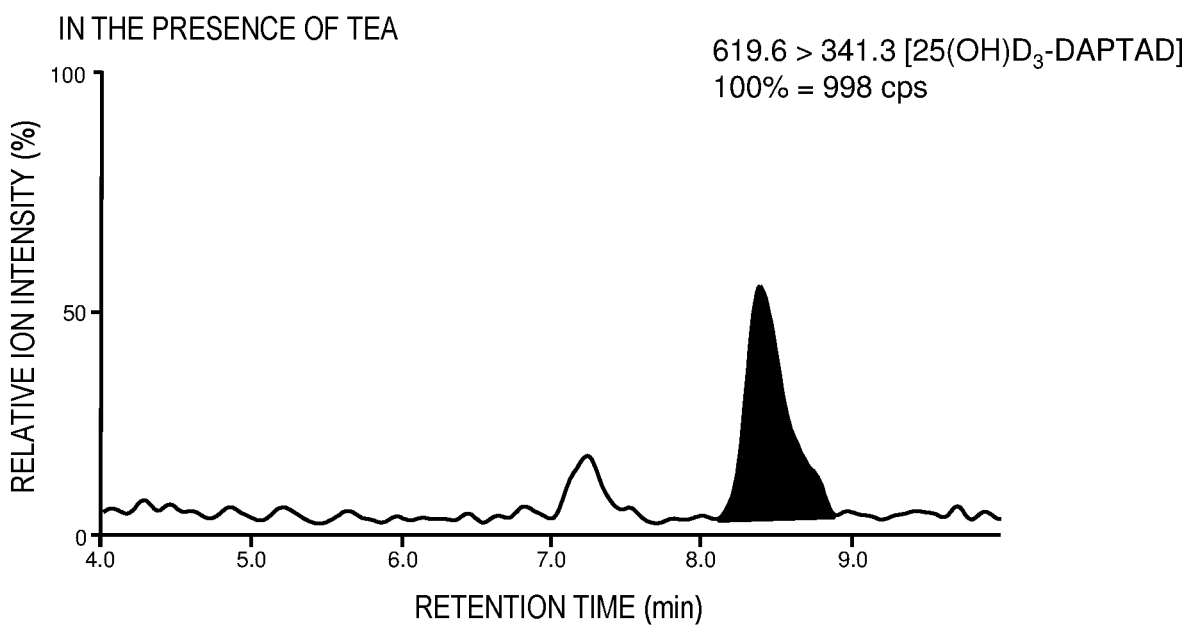
FIG. 15 is a mass chromatogram of $25(OH)D_3$-DAPTAD in the presence of triethylamine.
Figure 16:
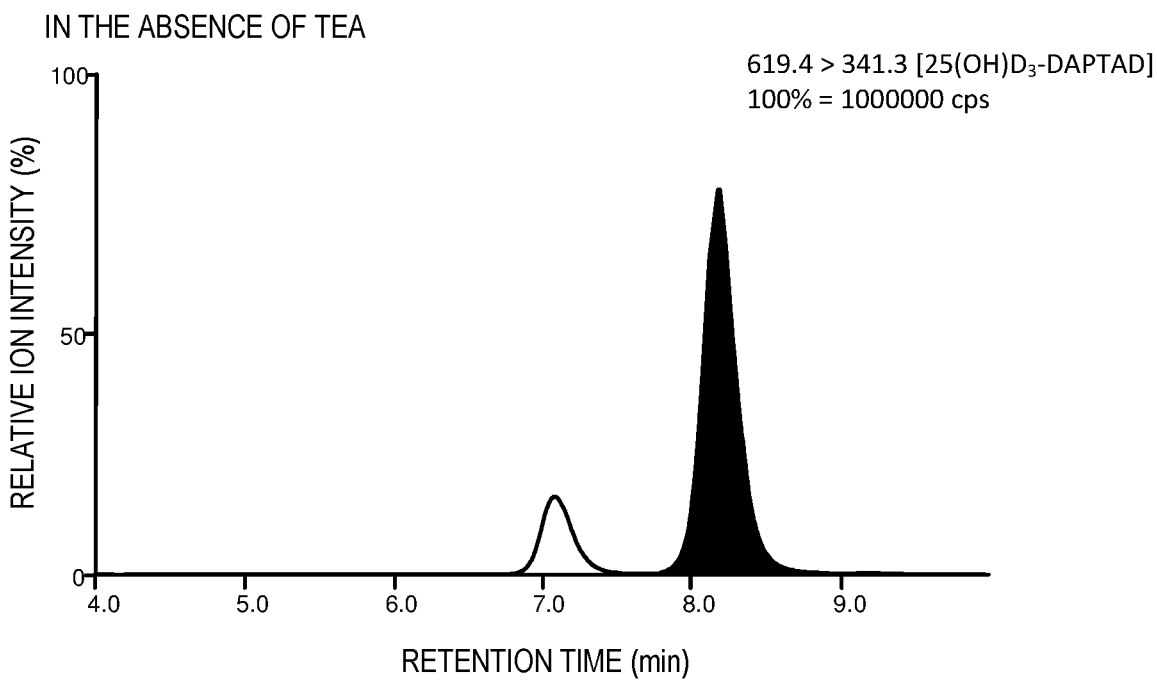
FIG. 16 is a mass chromatogram of $25(OH)D_3$-DAPTAD in the absence of triethylamine.
Figure 17:
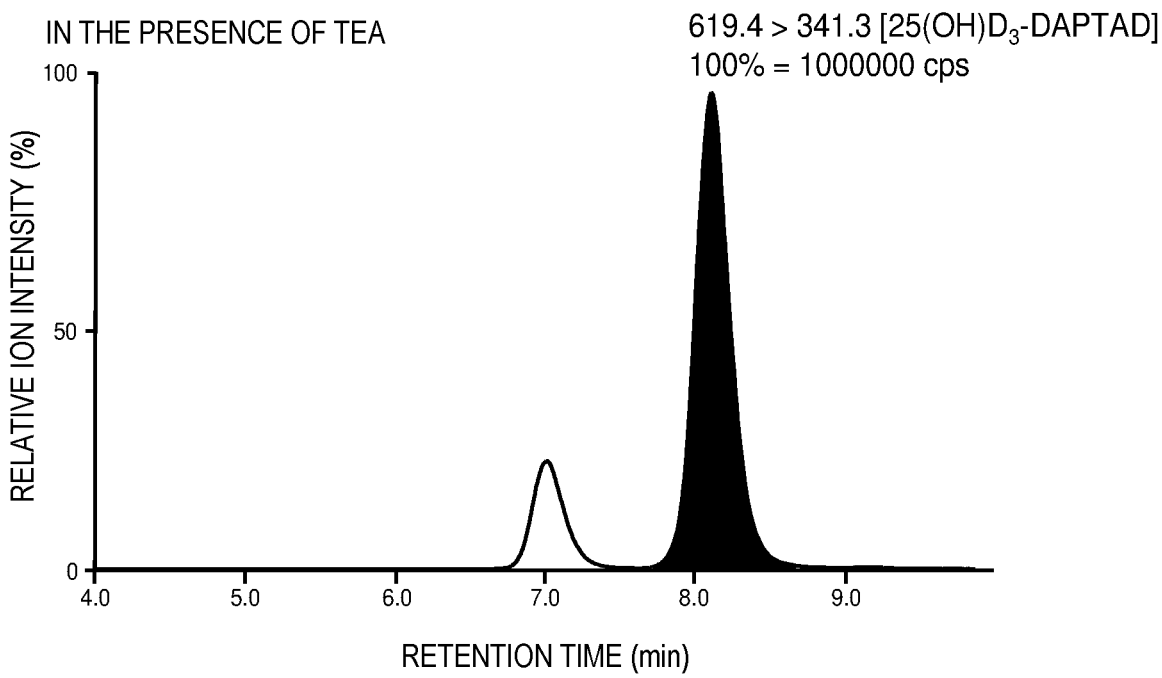
FIG. 17 is a mass chromatogram of $25(OH)D_3$-DAPTAD in the presence of triethylamine

FIG. 14 and FIG. 16 are mass chromatograms of examples in the absence of trimethylamine (TEA) as the decomposition inhibitor in the reaction stopping step of stopping the derivatization of 25(OH)D$_3$ with DAPTAD. FIG. 15 and FIG. 17 are mass chromatograms of examples in the presence of triethylamine as the decomposition inhibitor in the reaction stopping step of stopping the derivatization of 25(OH)D$_3$ with DAPTAD. In all examples, compounds other than 25(OH)D$_3$ are absence in the sample to be derivatized the analysis conditions are the same as above, and the observed transition is 25(OH)D$_3$-DAPTAD. Further, in FIG. 14 and FIG. 15, the sample equivalent to 2.5 pg was injected. In FIG. 16 and FIG. 17, the sample equivalent to 100 pg was injected.

First, comparing FIG. 14 and FIG. 15 in which the sample equivalent to 2.5 pg was injected, noise in the transition of 25(OH)D$_3$-DAPTAD in SRM measurement was reduced and a signal-to-noise-ratio (S/N ratio) was increased in FIG. 15 (Example 1) as compared to FIG. 14. This is considered the addition of triethylamine as the decomposition inhibitor in the derivatizing 25(OH)D$_3$ with DAPTAD suppress the decomposition of a 25(OH)D$_3$-DAPTAD and reduce the noise.

Further, comparing FIG. 16 and FIG. 17, in which the sample equivalent to 100 pg was injected, the relative intensity of a derivative was significantly reduced as compared to noise in FIG. 16 (Comparative Example 2). However, the relative intensity in the transition of 25(OH)D$_3$-DAPTAD in SRM measurement was increased in FIG. 17 (Example 2) as compared to FIG. 16 (Comparative Example 2).

As described above, the effect of inhibition the decomposition of 25(OH)D$_3$-DAPTAD was obtained by adding triethylamine as the decomposition inhibitor in the reaction stopping step of stopping the derivatization of 25(OH)D$_3$ with DAPTAD.

Next, description is given of the effect of adding triethylamine as the decomposition inhibitor in the reaction stopping step of derivatizing 25(OH)D$_3$S with DAPTAD as shown in FIG. 18 to FIG. 21.

Figure 18:
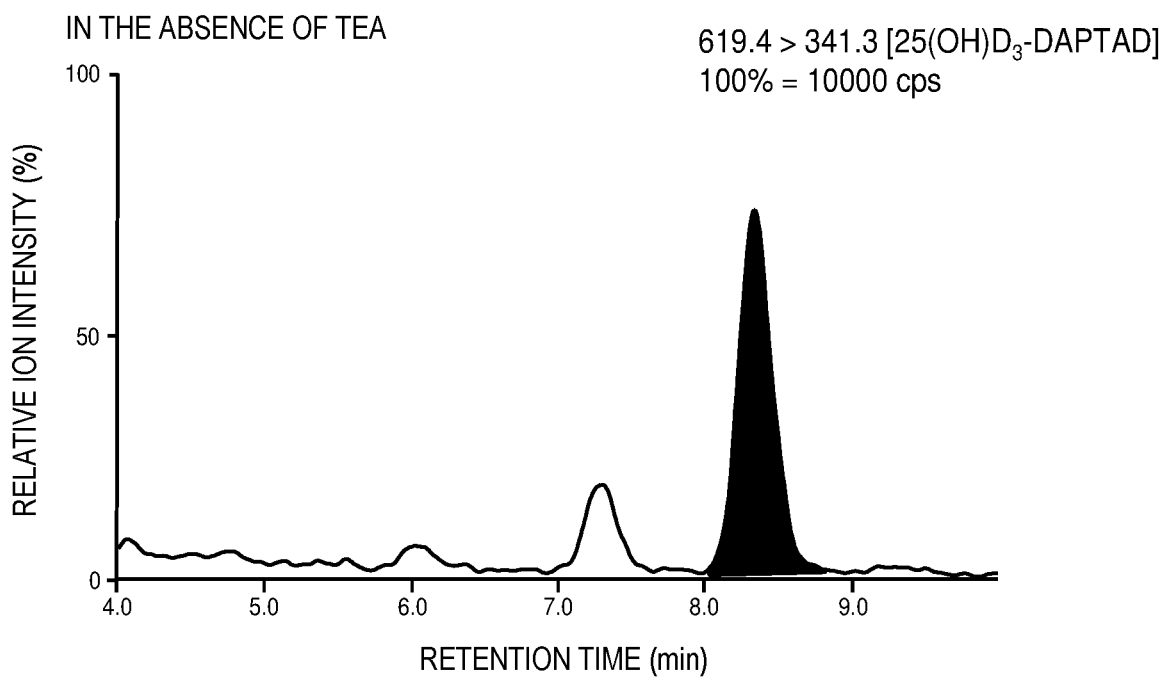
FIG. 18 is a mass chromatogram of $25(OH)D_3$-DAPTAD in the absence of triethylamine.
Figure 19:
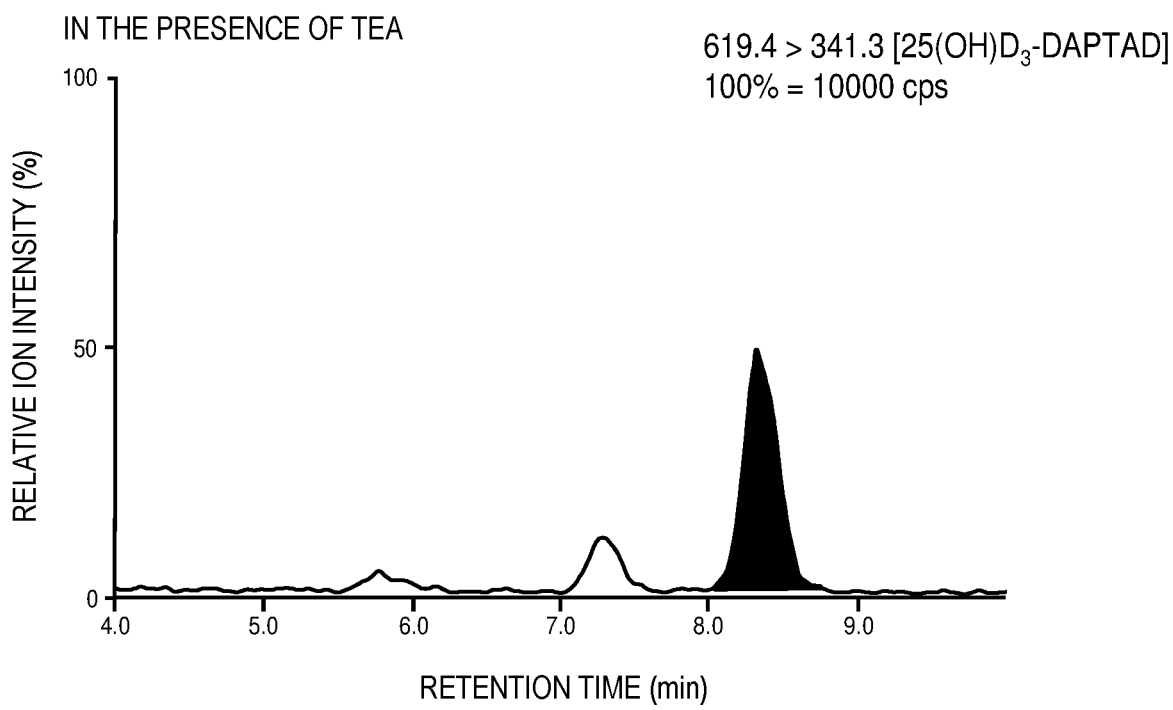
FIG. 19 is a mass chromatogram of $25(OH)D_3$-DAPTAD in the presence of triethylamine.
Figure 20:
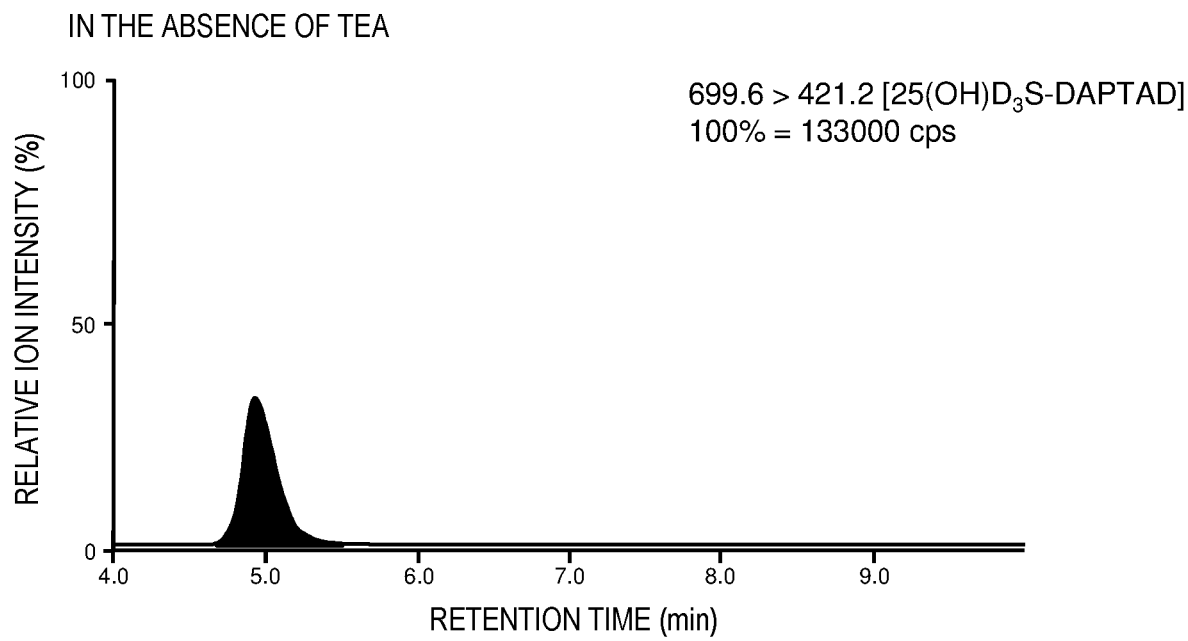
FIG. 20 is a mass chromatogram of $25(OH)D_3S$-DAPTAD in the absence of triethylamine.
Figure 21:
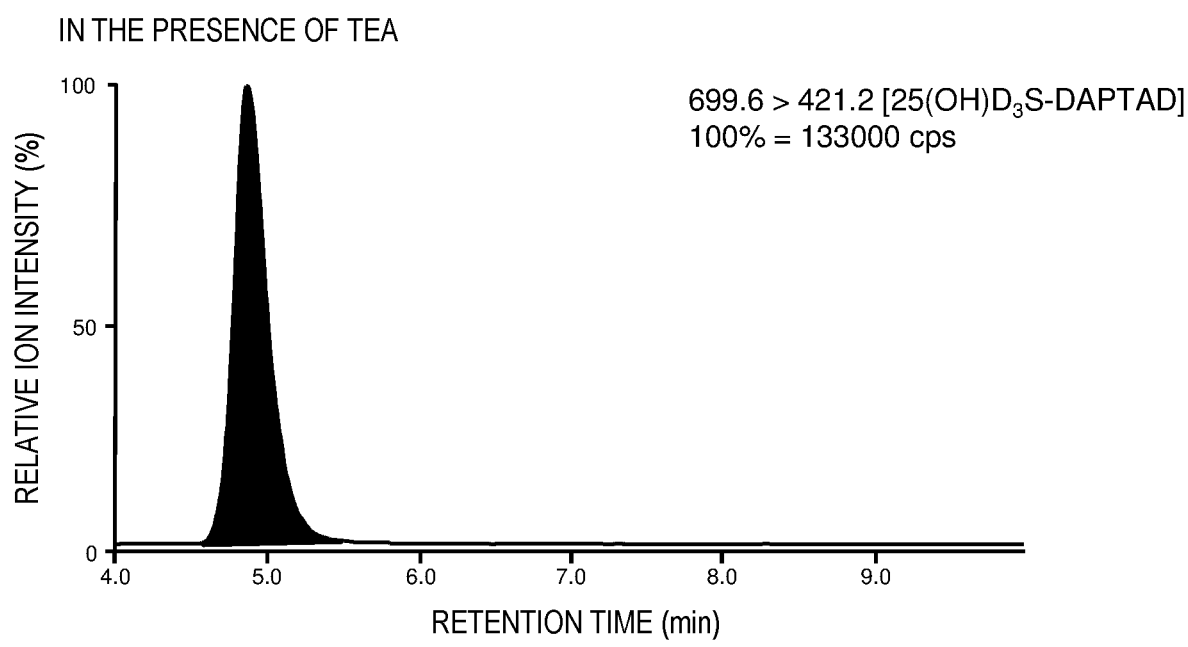
FIG. 21 is a mass chromatogram of $25(OH)D_3S$-DAPTAD in the presence of triethylamine.

FIG. 18 and FIG. 20 are mass chromatograms of examples in the absence of triethylamine as the decomposition inhibitor in the reaction stopping step of stopping the derivatization of 25(OH)D$_3$S with DAPTAD. FIG. 19 and FIG. 21 are mass chromatograms of examples in the presence of triethylamine as the decomposition inhibitor in the reaction stopping step of stopping the derivatization of 25(OH)D$_3$S with DAPTAD. In FIG. 18 and FIG. 20, the observed transition is 25(OH)D$_3$-DAPTAD. In FIG. 19 and FIG. 21, the observed transition is 25(OH)D$_3$S-DAPTAD. In all examples, compounds other than 25(OH)D$_3$S, for example, 25(OH)D$_3$ are absence in the sample to be derivatized, and the analysis conditions are the same as above.

Comparing FIG. 18 and FIG. 19, the ion intensity of the 25(OH)D$_3$-DAPTAD peak in FIG. 18 observed during a retention time of from 8.0 minutes to 9.0 minutes was higher than FIG. 19. Meanwhile, comparing FIG. 20 and FIG. 21, the ion intensity of 25(OH)D$_3$S-DAPTAD peak in FIG. 21 observed around a retention time of 5.0 minutes was higher than FIG. 20. From these, derivatizing 25(OH)D$_3$S with DAPTAD in the absence of triethylamine, 25(OH)D$_3$S-DAPTAD may decompose to 25(OH)D$_3$-DAPTAD through desulfoconjugation, however, in the presence of triethylamine the decomposition of 25(OH)D$_3$S-DAPTAD to 25(OH)D$_3$-DAPTAD is suppressed.

Both 25(OH)D$_3$S and 25(OH)D$_3$ are endogenous vitamin D metabolites, and both of them are object to be measured. As shown in FIG. 18 and FIG. 20, decomposition of a part of the 25(OH)D$_3$S-DAPTAD to 25(OH)D$_3$-DAPTAD makes accurate quantification of 25(OH)D$_3$S-DAPTAD difficult. Meanwhile, as shown in FIG. 20 and FIG. 21, in the presence of the decomposition inhibitor in the reaction stopping step, the decomposition of 25(OH)D$_3$S-DAPTAD is suppressed, and accurate quantification of 25(OH)D$_3$S-DAPTAD is possible.

Further, as shown in the results of FIG. 14 to FIG. 17, in the presence of triethylamine as the decomposition inhibitor in the reaction stopping step of derivatizing 25(OH)D$_3$ with DAPTAD, the effect of inhibition the decomposition of a derivative is also obtained, the ion intensity is not reduced. Therefore, in the case of a sample in which 25(OH)D$_3$ and 25(OH)D$_3$S coexist, adding triethylamine as the decomposition inhibitor in the reaction stopping step of stopping the derivatization with DAPTAD enables to quantify each of them with high accuracy, irrespective of whether any one of 25(OH)D$_3$ and 25(OH)D$_3$S is intended to be measured or both of them are intended to be measured simultaneously and to improve reliability of a measurement value.

As a result, even if 25(OH)D$_3$-DAPTAD and 25(OH)D$_3$S-DAPTAD may be decomposed with an oxidant (iodobenzene diacetate) that remained in the preparation of DAPTAD, the presence of triethylamine as the decomposition inhibitor in the reaction stopping step of stopping the DAPTAD derivatization enables to inhibit the decomposition of a derivative. Furthermore, the presence of triethylamine enables to enhance sensitivity and accuracy in the quantitative analysis of 25(OH)D$_3$-DAPTAD and 25(OH)D$_3$S-DAPTAD than before.

The present invention is not limited to the embodiments described above, and various modifications may be made thereto. For example, the present invention includes various other configurations substantially the same as the configurations described above in connection with the embodiments (e.g., a configuration having the same function, method, and results, or a configuration having the same objective and effects). The present invention also includes a configuration in which an unsubstantial element described above in connection with the embodiments is replaced by another element. The present invention also includes a configuration having the same actions and effects as those of the configurations described above in connection with the embodiments, or a configuration capable of achieving the same objective as that of the configurations described above in connection with the embodiments. The present invention further includes a configuration in which a known technology is added to the configurations described in connection with the embodiments.

Although only some embodiments of the present invention have been described in detail above, those skilled in the art would readily appreciate that many modifications are possible in the embodiments without materially departing from the novel teachings and advantages of the present invention. Accordingly, all such modifications are intended to be included within the scope of the present invention.

What is claimed is:

1. A reagent kit for quantifying vitamin D comprising:
   n types of 4-(4'-dimethylaminophenyl)-1,2,4-triazoline-3,5-dione (DAPTAD) isotopologues having different masses;
   a derivatization reaction stopping agent; and
   a decomposition inhibitor of a derivative;
   wherein the n types of DAPTAD isotopologues comprise at least three types of isotopologues that differ in mass by at least 3 Da from one another.

2. A method for quantifying vitamin D, with vitamin D contained in a biological sample being derivatized with a derivatization reagent and being measured with a mass spectrometer, the method comprising:
   derivatizing an n number of biological samples comprising vitamin D by using n types of 4-(4'-dimethylaminophenyl)-1,2,4-triazoline-3,5-dione (DAPTAD) isotopologues as derivatization reagents, resulting in n number of biological samples comprising vitamin D derivatives;

mixing the n number of biological samples comprising vitamin D derivatives, resulting in a mixed sample containing n number of types of vitamin D derivatives; and subjecting the n number of types of vitamin D derivatives in the mixed sample to quantitative analysis using the mass spectrometer, wherein the mass spectrometer is a tandem mass spectrometer, and the quantitative analysis comprises:

separating the n number of types of vitamin D derivatives in the mixed sample by high-performance liquid chromatograph to obtain separated samples;

ionizing the separated samples;

selecting a precursor ion by separating ions formed in the ionizing, according to mass;

cleaving a precursor ion and generating one or more fragment ions;

separating the one or more fragment ions according to mass; and detecting an amount of the separated one or more fragment ions and associating the detected amount with an amount of vitamin D contained in the biological samples, wherein the vitamin D in the biological samples comprises a molecular species of vitamin D comprising sulfate, and wherein the molecular species of vitamin D comprising sulfate is derivatized with the derivatization reagents and subjected to the quantitative analysis, and wherein the n types of DAPTAD isotopologues comprise at least three types of isotopologues that differ in mass by at least 3 Da from one another.

3. The method of claim 2, wherein the at least three types of isotopologues that differ in mass by at least 3 Da from one another comprise $^2H_0$-DAPTAD, $^2H_3$-DAPTAD, and $^2H_6$-DAPTAD.

4. The method of claim 2, wherein the vitamin D derivatives comprise derivatized 25-hydroxy vitamin $D_3$; and wherein a precursor ion of the derivatized 25-hydroxy vitamin $D_3$ has a mass/charge ratio of 619.5±0.5.

5. The method of claim 2, wherein the vitamin D derivatives comprise derivatized 25-hydroxy vitamin D3 and one or more fragment ions of the derivatized 25-hydroxy vitamin $D_3$ comprise an ion having a mass/charge ratio of 341.3±0.5.

6. The method of claim 2, wherein the molecular species of vitamin D comprising sulfate is 25-hydroxy vitamin $D_3$-3β-sulfate; and wherein a precursor ion of a derivatized-25-hydroxy vitamin $D_3$-3β-sulfate has a mass/charge ratio of 699.6±0.5.

7. The method of claim 2, wherein 25-hydroxy vitamin $D_3$ is used as an internal standard substance.

8. The method of claim 2, wherein the detecting the amount of the separated one or more fragment ions is a detection using multiple reaction monitoring (MRM) or selected reaction monitoring (SRM).

9. The method of claim 2, wherein the derivatizing comprises stopping a derivatization reaction of vitamin D, and wherein a decomposition inhibitor to inhibit decomposition of a derivative to be obtained is added when stopping the derivatization reaction of vitamin D.

\* \* \* \* \*

UNITED STATES PATENT AND TRADEMARK OFFICE
CERTIFICATE OF CORRECTION

PATENT NO. : 11,193,948 B2
APPLICATION NO. : 15/813542
DATED : December 7, 2021
INVENTOR(S) : Tatsuya Higashi et al.

It is certified that error appears in the above-identified patent and that said Letters Patent is hereby corrected as shown below:

In the Claims

Column 24, Line 57, Claim 1, delete "derivative;" and insert -- derivative, --

Column 26, Line 13, Claim 5, delete "D3" and insert -- $D_3$ --

Column 26, Lines 17-18, Claim 6, delete "derivatized-25-hydroxy"

Signed and Sealed this
Ninth Day of August, 2022

Katherine Kelly Vidal
*Director of the United States Patent and Trademark Office*